US009708608B2

(12) United States Patent
Collombat et al.

(10) Patent No.: US 9,708,608 B2
(45) Date of Patent: Jul. 18, 2017

(54) METHODS FOR PRODUCING A POPULATION OF PANCREATIC BETA-CELLS

(71) Applicants: INSERM (INSTITUT NATIONAL DE LA SANTE ET DE LA RECHERCHE MEDICALE), Paris (FR); CENTRE NATIONAL DE LA RECHERCHE SCIENTIFIQUE (CNRS), Paris (FR); UNIVERSITE NICE SOPHIA ANTIPOLIS, Nice (FR)

(72) Inventors: Patrick Collombat, Nice (FR); Keith Al-Hasani, Nice (FR); Monica Courtney, Nice (FR); Nouha Ben-Ohtman, Nice (FR); Elisabet Gjernes, Nice (FR); Ahmed Mansouri, Goettingen (DE)

(73) Assignees: Institut National de la Sante et de la Recherche Medicale (INSERM), Paris (FR); Centre National de la Recherche Scientific (CNRS), Paris (FR); Universite Nice Sophia Antipolis, Nice (FR)

( * ) Notice: Subject to any disclaimer, the term of this patent is extended or adjusted under 35 U.S.C. 154(b) by 0 days.

(21) Appl. No.: 14/431,857

(22) PCT Filed: Sep. 16, 2013

(86) PCT No.: PCT/EP2013/069181
§ 371 (c)(1),
(2) Date: Mar. 27, 2015

(87) PCT Pub. No.: WO2014/048788
PCT Pub. Date: Apr. 3, 2014

(65) Prior Publication Data
US 2015/0240235 A1 Aug. 27, 2015

(30) Foreign Application Priority Data

Sep. 27, 2012 (EP) .................................... 12306172

(51) Int. Cl.
C12N 5/071 (2010.01)
C12N 15/113 (2010.01)
A61K 31/197 (2006.01)
A01K 67/027 (2006.01)
A61K 45/06 (2006.01)
A61K 31/713 (2006.01)
A61K 31/00 (2006.01)

(52) U.S. Cl.
CPC ........ *C12N 15/113* (2013.01); *A01K 67/0276* (2013.01); *A61K 31/00* (2013.01); *A61K 31/197* (2013.01); *A61K 31/713* (2013.01); *A61K 45/06* (2013.01); *C12N 5/0676* (2013.01); *A01K 2217/075* (2013.01); *A01K 2217/206* (2013.01); *A01K 2227/105* (2013.01); *A01K 2267/0362* (2013.01); *C12N 2310/11* (2013.01); *C12N 2310/12* (2013.01); *C12N 2310/14* (2013.01); *C12N 2320/30* (2013.01); *C12N 2501/60* (2013.01); *C12N 2501/845* (2013.01)

(58) Field of Classification Search
CPC ............ C12N 5/0676; C12N 2501/845; C12N 2506/07
See application file for complete search history.

(56) References Cited

U.S. PATENT DOCUMENTS

2010/0166675 A1 7/2010 Wang et al.

FOREIGN PATENT DOCUMENTS

WO 2011/012707 A1 2/2011

OTHER PUBLICATIONS

Collombat et al. The extopic expression of Pax4 in the mouse pancreas converts progenitor cells into alpha and subsequently beta cells. Cell, vol. 138, pp. 449-462, 2009.*
Mamin et al. Activin a decreases glucagon and arx gene expression in alpha-cell lines. Molecular Endocrinology, vol. 21, No. 1, pp. 259-273, 2007.*
Bailey et al. Glucose-dependent regulation of gamma-aminobutyric acid (GABAA) receptor expression in mouse pancreatic islet alpha-cells. Diabetes, vol. 59, pp. 320-327, Feb. 2007.*
Itoh et al. Partial loss of pancrease endocrine and exocrine cells of human ARX-null mutation: Consideration of pancreas differentiation. Differentiation, vol. 80, pp. 118-122, 2010.*
Kordowich et al., "Reprogramming into pancreatic endocrine cells based on developmental cues", Molecular and Cellular Endocrinology, Jul. 8, 2010, pp. 62-69, vol. 323, No. 1.
Dhawan et al., "Pancreatic Cell Identity Is Maintained by DNA Methylation-Mediated Repression of Arx", Developmental Cell, Mar. 18, 2011, pp. 419-429, vol. 20, No. 4.
Hancock et al., "Glucagon Deficiency Reduces Hepatic Glucose Production and Improves Glucose Tolerance in Adult Mice", Molecular Endocrinology, Aug. 1, 2010, pp. 1605-1614, vol. 24, No. 8.

(Continued)

*Primary Examiner* — Jennifer Dunston
(74) *Attorney, Agent, or Firm* — Whitham Curtis & Cook, PC

(57) ABSTRACT

The present invention relates to an in vitro or ex vivo method for producing a population of pancreatic beta-cells, comprising the step of inhibiting the expression or the activity of Arx in a population of pancreatic alpha-cells. The present invention also relates to method for inducing the conversion of pancreatic alpha-cells in pancreatic beta-cells in a patient in need thereof.

7 Claims, 6 Drawing Sheets

(56) References Cited

OTHER PUBLICATIONS

Figure 1:
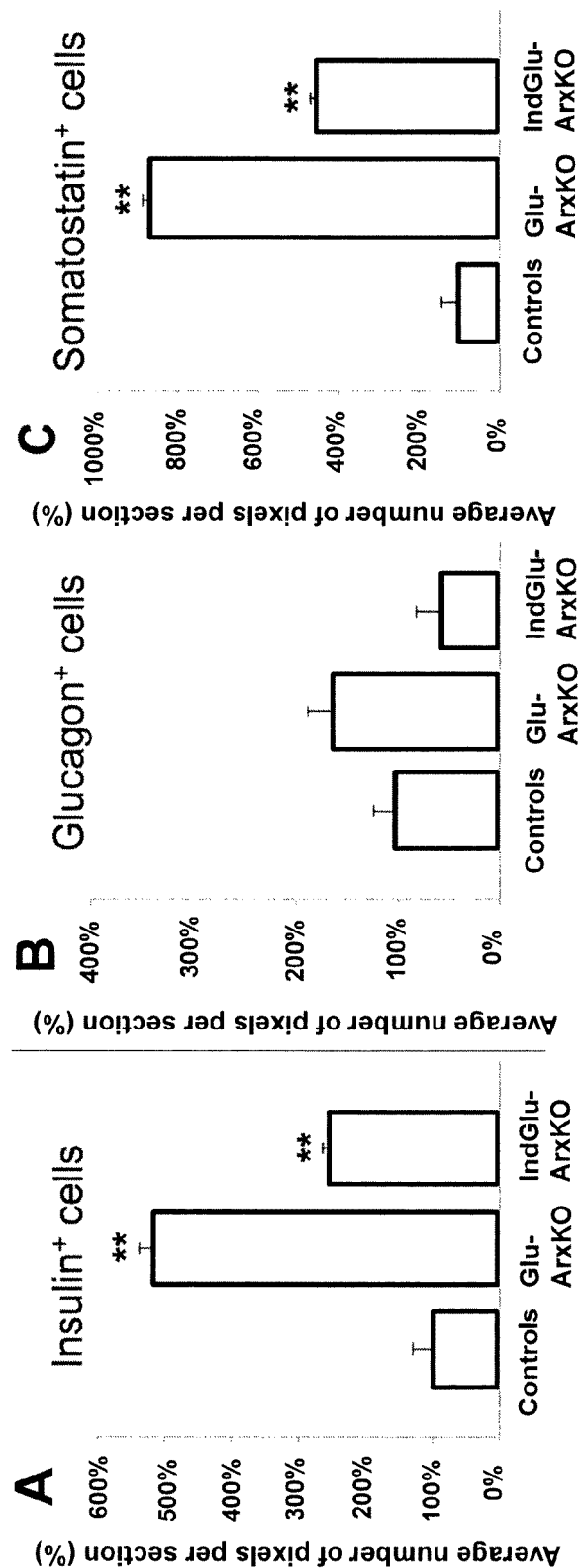

Courtney et al., "In vivo conversion of adult [alpha]-cells into [beta]-like cells: a new research avenue in the context of type 1 diabetes", Diabetes, Obesity & Metabolism, Oct. 2011, pp. 47-52, vol. 13, Suppl 1.
Collombat et al., "The Simultaneous Loss of ARX and PAX4 Genes Promotes a Somatostatin-Producing Cell Fate Specification At the Expense of the [Alpha]- and [Beta]-Cell Lineages in the Mouse Endocrine Pancreas", Development, Jul. 1. 2005, pp. 2969-2980, vol. 132, No. 13.
Collombat et al., "Embryonic endocrine pancreas and mature [beta] cells acquire [alpha] and PP cell phenotypes upon Arx misexpression", Journal of Clinical Investigation, Apr. 2, 2007, pp. 961-970, vol. 117, No. 4.
Shin et al., "Aristaless-related homeobox gene disruption leads to abnormal distribution of GABAergic interneurons in human neocortex: evidence based on a case of X-linked lissencephaly with abnormal genitalia", Acta Neuropathaologica, May 6, 2008, pp. 453-462, vol. 116, No. 4.
Friocourt et al., "Mutations in ARX result in several defects involving GABAergic neurons", Frontiers in Cellular Neuroscience, Mar. 2010, pp. 1-11, vol. 4.
Soltani et al, "GABA exerts protective and regenerative effects on islet beta cells and reverses diabetes", Proceedings of the National Academy of Sciences, Jun. 27, 2011, pp. 11692-11697, vol. 108, No. 28.
Courtney et al., "The Inactivation of Arx in Pancreatic alpha-Cells Triggers Their Neogenesis and Conversions into Functional beta-Like Cells", PLOS Genetics, Oct. 31, 2013, pp. e1003934, vol. 9, No. 10.

\* cited by examiner

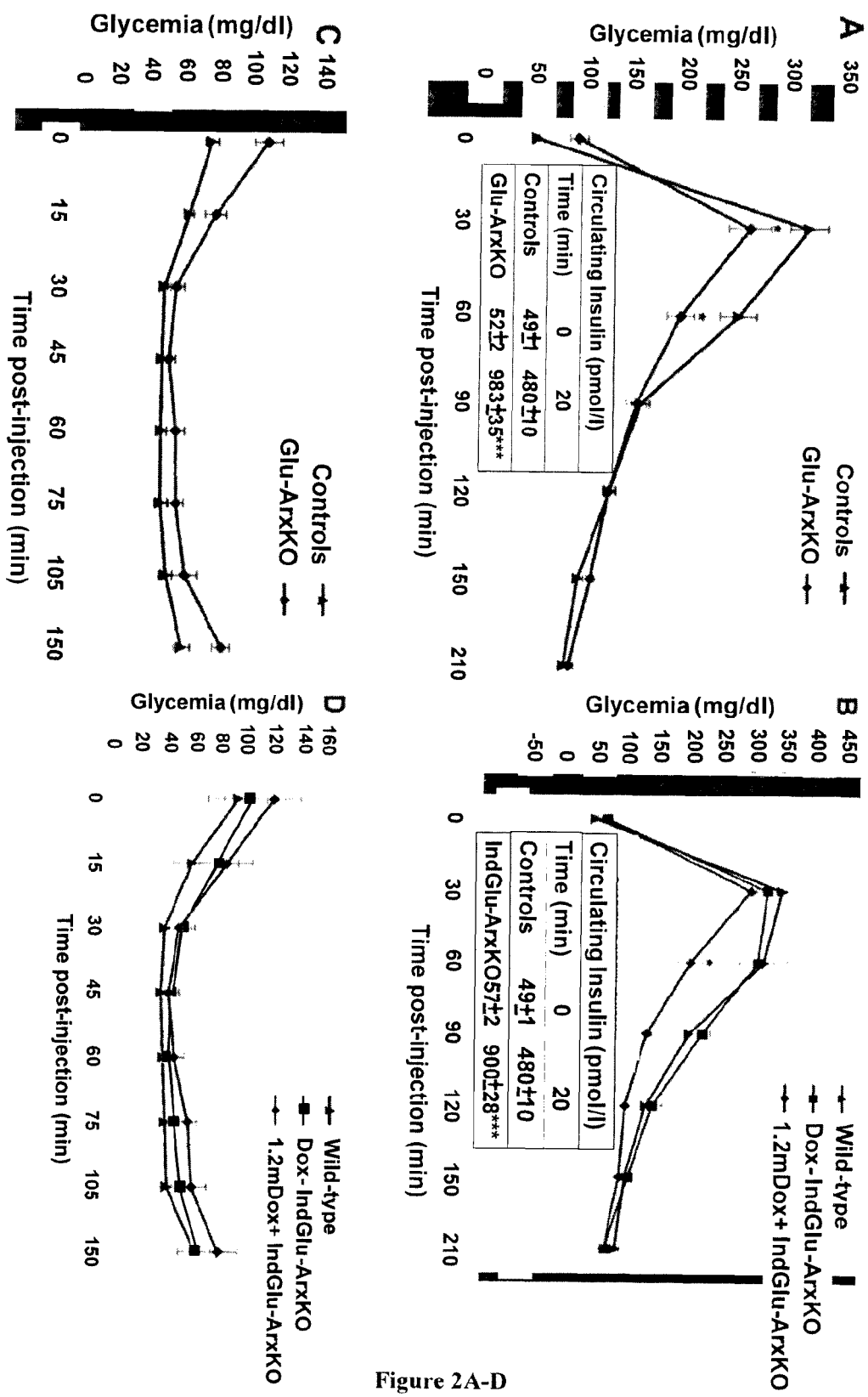
Figure 2A-D

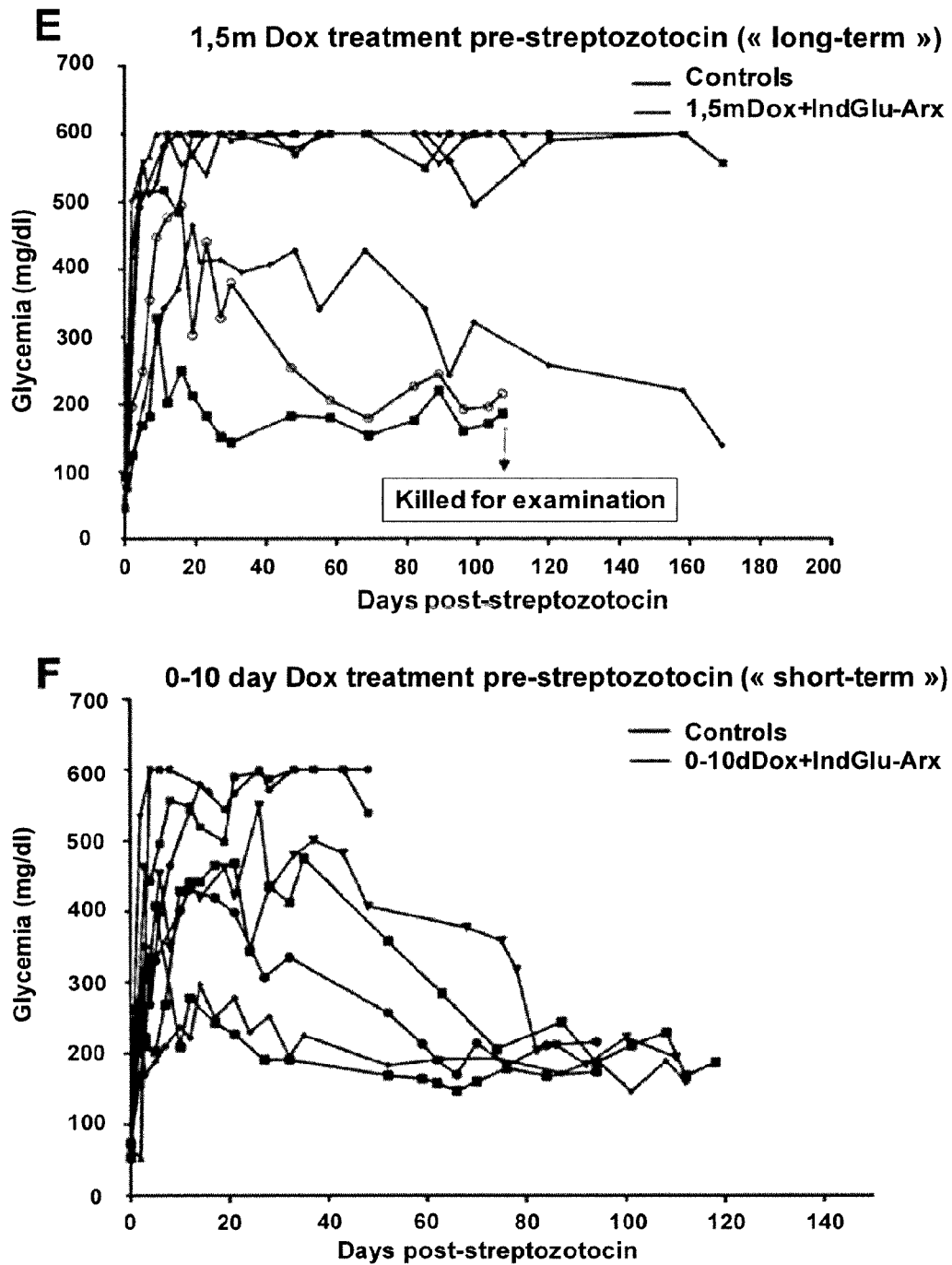
Figure 2E-F

METHODS FOR PRODUCING A POPULATION OF PANCREATIC BETA-CELLS

FIELD OF THE INVENTION

The present invention relates to methods for the production of pancreatic beta-cells as well as to methods for the screening of compounds inducing a pancreatic beta-cell phenotype. The present invention also relates to method for inducing the conversion of pancreatic alpha-cells in pancreatic beta-cells in a patient in need thereof.

BACKGROUND OF THE INVENTION

The pancreas is composed of two morphologically distinct compartments: exocrine cells, encompassing acinar and duct cells, and the endocrine tissue (reviewed in Slack, 1995). The endocrine compartment represents less than 2% of the organ and consists of five hormone-synthesising cell types: the insulin-secreting β-cells, the glucagon-secreting α-cells, the somatostatin-secreting δ-cells, pancreatic polypeptide-secreting PP-cells and the ghrelin-secreting ε-cells. These endocrine cells are organised into highly vascularised functional units called islets of Langerhans that are involved in glucose homeostasis. Pancreatic development corresponds to an elaborate process of morphological events accompanied by a complex pattern of cellular differentiation and lineage selection. These events are mediated in great part by tissue interactions, signalling pathways and directed cascades of gene expression that determine cell fate. Thus, Pdx1 plays a critical role in early pancreas development: removal of PDX1 by gene targeting arrests pancreatic development after initial bud formation. The specification of endocrine cells in the developing pancreatic endoderm depends on appropriate Notch signalling and expression of the pro-endocrine basic helix-loop-helix (bHLH) transcription factor neurogenin 3 (Ngn3), a member of the neurogenin/neuroD family of pro-neuronal genes. Endocrine cell fate allocation largely depends on the interplay between the transcription factors Arx and Pax4. These were shown to display antagonistic activities in the processes underlying the specification of the endocrine subtype destinies through an inhibitory cross-regulatory circuit that controls the transcriptional state of these two genes (Collombat et al., 2005). The expression of Arx was found to be upregulated in the absence of a functional Pax4 allele and vice versa (augmentation of the Pax4 transcript content in Arx mutants), suggesting that normal endocrine specification requires the prevalence of either factor in order to specify a particular endocrine cell subtype; if Pax4 predominates, the β- and δ-cell fates will be specified, whereas Arx will favour the α-cell commitment. Lastly, Arx and Pax4 were found to mutually inhibit each other's transcription through direct physical interaction with the pertinent promoter (Collombat et al., 2005). The persistent expression of Arx in early pancreatic and/or endocrine precursor cells during embryonic development resulted in a dramatic reduction in β- and δ-cell numbers, concurrent with an increase in α- and PP-cell populations (Collombat et al., 2007). These results indicated that Arx is thereby sufficient to promote the α- and PP-lineages during pancreas morphogenesis. More interestingly, the misexpression of Arx in adult β-cells was found to induce their conversion into cells exhibiting α- or PP-cell characteristics (Collombat et al., 2007). This discovery was of fundamental importance in the context of β-cell-based therapy, as it implied that the complementary conversion might be achieved, that is, to generate β-cells from alternative endocrine cells. Accordingly, the ectopic expression of Pax4 in the developing mouse pancreas resulted in oversized islets mostly composed of cells displaying a β-cell phenotype (Collombat et al., 2009), indicating that Pax4 misexpression is sufficient to promote the β-cell lineage allocation during the development. Importantly, the misexpression of Pax4 in glucagon-expressing cells, coupled with genetic labelling to follow their outcome, resulted in a loss of α-cells concurrently with a dramatic increase in the number of insulin-producing cells. Lineage tracing experiments demonstrated a conversion of glucagon-positive cells into insulin-expressing cells. Moreover, the newly generated insulin-expressing cells showed most of the features of true β-cells (Collombat et al., 2009).

Accordingly, international patent application WO 2011/012707 describes a method for producing a population of pancreatic beta-cells, comprising the step of providing at least one pancreatic alpha-cell or at least one precursor cell with Pax4 or a nucleic acid encoding Pax4. However, due to (1) the mutual inhibitory interplay occurring between Pax4 and Arx and (2) the expression of Arx in glucagon-producing cells, it remains to determine whether the ectopic expression of Pax4 in glucagon-expressing cells and the ensuing α-to-β-like cell conversion were directly caused by Pax4 or by the subsequent inhibition of Arx expression. Furthermore, it should be reminded that hitherto Arx and Pax4 have only been shown to mutually inhibit during embryogenesis and particularly during the genesis of the pancreas and never in adult pancreatic beta-cells (Kordowich et al., 2011).

The regenerative capacity of pancreatic alpha-cells (or glucagon-producing cells), and their potential for conversion into β-like cells by the simple ectopic expression of Pax4, are of interest in the context of T1D research. However, this transgenic approach would be unfeasible for the development of human-targeted therapies.

Thus, the possibility to produce β-cells from α-cells by directly inhibiting Arx in said cells (e.g. in adult β-cells) has not been experimentally demonstrated nor even suggested, whereas there is need for an easy and safe method that generates β-cells that can be used in the therapeutic field (in vivo) as well as in the screening field (in vitro). Additionally, identifying small compounds mimicking the effects of the inhibition of Arx and/or inducing the conversion of pancreatic alpha-cells in pancreatic beta-cells is highly required.

Over the past decades, numerous studies have uncovered a role for γ-aminobutyric acid (GABA) in the endocrine pancreas and in diabetes mellitus. GABA, synthesized from glutamate by glutamic acid decarboxylase (GAD) in β-cells, is an extracellular signaling molecule in the pancreatic islets. Once released, GABA is thought to serve as a functional regulator of pancreatic hormone secretion or as a fast-acting paracrine signaling molecule for the communication between β-cells and the other endocrine cells in the islets of Langerhans. The presence of $GABA_B$ receptors in β-cells and of $GABA_A$ receptors in α-cells supports the putative autocrine/paracrine role of locally secreted GABA in islets. Indeed, the GABA regulation of hormone secretion was shown to be mediated by its receptors. Interestingly, GAD (the enzyme involved in GABA synthesis) was found to be one of the major autoantigens in T1D and GABA was found to be decreased in endocrine pancreatic tissue in experimental and human diabetes. These findings clearly indicate that the GABA network is altered in T1D but its role in this pathology remains to be clarified. In addition, several studies have demonstrated that GABA participates in maintaining β-cell mass (Mendu et al., 2011; Soltani et al., 2011), inducing β-cell proliferation and protecting β-cells from apoptosis in vitro (Soltani et al., 2011; Ligon et al., 2007). Interestingly, it was shown that GABA could decrease blood glucose levels and exert protective and regenerative effects on the β-cell mass in streptozotocin-induced diabetes in mice (Soltani et al., 2011; Gomez et al., 2007). GABA was also found to reverse diabetes in NOD mice (Soltani et al., 2011; Tian et al., 2011). The suggested explanation was that GABA might act in an autocrine/paracrine manner to regenerate the pancreatic islets via β-cell proliferation.

SUMMARY OF THE INVENTION

In a first aspect, the present invention provides an in vitro or ex vivo method for producing a population of pancreatic beta-cells, comprising the step of inhibiting the expression or the activity of Arx in a population of pancreatic alpha-cells.

In a second aspect, the present invention relates to a population of pancreatic beta-cells obtainable by the above mentioned method.

Such population of pancreatic beta-cells is useful in a pharmaceutical composition, where they are in combination with a pharmaceutically acceptable carrier.

In a third aspect, the invention relates to a population of pancreatic alpha-cells which do not express Arx or in which the expression or activity of Arx is abolished or inhibited.

In a fourth aspect, the present invention relates to an inhibitor of Arx gene expression for use in the prevention or the treatment of diabetes in a subject in need thereof, wherein said inhibitor of Arx gene expression is a siRNA oligonucleotide, a ribozyme, or an antisense oligonucleotide as well as to a pharmaceutical composition comprising such inhibitor of Arx gene expression.

In a fifth aspect, the present invention relates to a method for the screening of a pancreatic-beta-cell phenotype-inducing compound, comprising the steps of a) contacting at least one pancreatic alpha-cell with a given compound, and b) testing whether said compound is capable of inhibiting Arx gene expression.

In a sixth aspect, the present invention relates to an inhibitor of Arx gene expression for use in a method for inducing the conversion of pancreatic alpha-cells in pancreatic beta-cells in a patient in need thereof.

In a last and seventh aspect, the present invention relates to pharmaceutical composition or a kit-of-part composition comprising an inhibitor of Arx gene expression and an immunosuppressive agent for use in a method improving the survival of regenerated pancreatic beta-cells in a patient in need thereof.

DETAILED DESCRIPTION OF THE INVENTION

The inventors have now shown that immature and adult β-cells can be converted in vivo into functional insulin-expressing cells upon the sole inactivation of Arx in these same cells by using two mouse lines allowing the conditional inactivation of Arx expression in glucagon-expressing cells, the first using a classical Cre-LoxP approach whereas the second allows the inducible and selective ablation of Arx. In addition, a cycle of endocrine cell regeneration is initiated accompanied by islet neogenesis, through a process involving the reactivation of the pro-endocrine gene Ngn3. Interestingly, newly formed insulin-expressing cells, originating from previously glucagon-expressing cells were observed following chemically-induced β-cell ablation opening a new opportunity for the therapeutic field.

Here, combining conditional loss-of-function and lineage tracing approaches, the inventors show that the selective inhibition of Arx in α-cells, the antagonist of Pax4, is sufficient to promote the conversion of adult α-cells into β-like cells at any age. Interestingly, this conversion induces compensatory processes resulting in a continuous α-cell neogenesis, such cells being subsequently converted into β-like cells upon Arx inhibition. Of interest, through the generation and analysis of Arx and Pax4 conditional double-mutants, they provide evidence that Pax4 is dispensable for these regeneration processes, indicating that Arx represents the main trigger of α-cell-mediated β-like cell neogenesis. Importantly, the loss of Arx in α-cells is sufficient to regenerate the whole β-cell mass following toxin-induced diabetes. These new results highlight that only the inhibition of Arx expression is required for the α-to-β-like cell conversion.

Moreover, the inventors have now shown that GABA has an effect on the inhibition of the expression of Arx in α-cells leading to their conversion in β-cells. To address this issue, both wild-type (WT) and, for lineage tracing purposes, Glu-Cre::Rosa26-lox-β-gal mice were treated with GABA. They provide evidence that glucagon-expressing cells may, upon GABA addition, be converted into functional insulin-producing cells, leading to islet hypertrophy due to a β-cell hyperplasia. A cycle of endocrine cell regeneration is subsequently activated accompanied by islet neogenesis, such a process involving the reactivation of the pro-endocrine gene Ngn3. Lastly, following streptozotocin treatment and upon GABA addition, β-like cells are regenerated, these deriving from cells that expressed the glucagon hormone.

The inventors have thus shown that long-term administration of an inhibitor of the expression or the activity of Arx (such as an antisense oligonucleotide or a siRNA against Arx, GABA or a GABA receptor agonist) induces successive cycles of endocrine cell regeneration by promoting the proliferation of cells within the ductal epithelium/lining, such cells re-expressing the pro-endocrine factor Ngn3 and being successively converted into a and β-like cell. Moreover, the long-term administration of such inhibitor of the expression or the activity of Arx may be combined with a simultaneous or subsequent administration of an immunosuppressive agent currently used in diabetes in order to protect the in vivo newly generated functional insulin-producing cells. Accordingly, the inventors have developed a method for inducing the conversion of pancreatic alpha-cells in pancreatic beta-cells in a patient in need thereof in a sufficient number in order to produce enough insulin in said patient but also for improving the survival of said new pancreatic β-cells and hence maintaining the number of these beta-cells for a long-term benefit for the patient.

Definitions

Throughout the specification, several terms are employed and are defined in the following paragraphs.

As used herein, the term "pancreatic beta-cells", "beta-cells" or "insulin-secreting beta-cells" are used interchangeably and refer to cells capable of producing insulin upon stimulation with glucose. More preferably, the expression of specific surface antigens is used to determine whether a cell is a pancreatic beta-cell. For instance, pancreatic beta-cells express the glucose transporter, Glut2. Alternatively, the expression of specific transcription factors is used to determine whether a cell is a pancreatic beta-cell. For instance, pancreatic beta-cells highly express the transcription factors Pdx1, Nkx6.1, MafA and Pax4. Lastly, electron microscopy observation can be used to ascertain a typical beta-cell ultrastructure.

As used herein, the terms "pancreatic alpha-cells", "alpha-cells" or "glucagon-expressing cells" are used interchangeably and refer to cells capable of expressing glucagon as a consequence of decreased blood sugar levels. More preferably, the expression of specific transcription factors is used to determine whether a cell is a pancreatic alpha-cell. For instance, pancreatic alpha-cells express the transcription factor Arx, Brn-4 and MafA. Lastly, electron microscopy observation can be used to ascertain a typical alpha-cell ultrastructure.

As used herein, the term "Arx" refers to the Aristaless related homeodomain protein which is well known in the art. The Arx gene is part of a larger family of homeobox genes, which act during early embryonic development to control the formation of many body structures. The Arx protein is thus involved in the development of the pancreas. The naturally occurring human Arx gene has a nucleotide sequence as shown in GENBANK® (a genetic sequence database) Accession number NM_139058.2 and the naturally occurring human Arx protein has an aminoacid sequence as shown in GENBANK® Accession number NP_620689.1. The murine nucleotide and amino acid sequences have also been described (GENBANK® Accession numbers NM_007492.3 and NP_031518.2).

As used herein, the terms "isolated" or "purified", when referring to a cell or a population of cells, mean that said cell or said population of cells is present in the substantial absence of other cells or population of cells. The terms "isolated" or "purified" as used herein preferably mean at least 75% by weight or number, more preferably at least 85% by weight or number, still preferably at least 95% by weight or number, and most preferably at least 98% by weight or number, of cells of the same type are present.

As used herein, the term "receptor agonist" refers to the native ligand of that receptor (e.g., a GABA receptor) to analogues thereof or other ligands that similarly "activate" the receptor, and/or to a positive allosteric modulator of the receptor.

As used herein, the term "GABA" refers to gamma-amino butyric acid of formula (I) or a pharmaceutically acceptable salt, solvate or prodrug thereof as well as mixtures thereof:

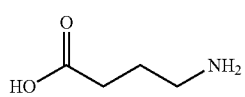

(I)

As used herein, the term "$GABA_A$ receptor specific agonist" refers to an agent that has agonistic activity at the $GABA_A$ receptor and substantially no agonist activity at the $GABA_B$. A "$GABA_A$ receptor preferential agonist" refers to an agent that has greater agonistic activity at the $GABA_A$ receptor than at the $GABA_B$. Typically, the $GABA_A$ receptor preferential agonist has at least 1.2-fold, more preferably at least 1.5 fold still more preferably at least 2 fold, and most preferably at least 3-fold, at least 5-fold, or at least 10-fold greater activity at the $GABA_A$ receptor than at the $GABA_B$ and as determined using an conventional assay for agonist activity at a GABA receptor.

As used herein, the term "$GABA_B$ receptor specific agonist" refers to an agent that has agonistic activity at the $GABA_B$ receptor and substantially no agonist activity at the $GABA_A$. A "$GABA_B$ receptor preferential agonist" refers to an agent that has greater agonistic activity at the $GABA_B$ receptor than at the $GABA_A$. In certain embodiments the $GABA_B$ receptor preferential agonist has at least 1.2-fold, more preferably at least 1.5 fold still more preferably at least 2 fold, and most preferably at least 3-fold, at least 5-fold, or at least 10-fold greater activity at the $GABA_B$ receptor than at the $GABA_A$ as determined using an conventional assay for agonist activity at a GABA receptor.

Methods for Producing a Population of Pancreatic Beta-cells

The inventors have demonstrated that it is possible to produce pancreatic beta-cells, by inactivating in pancreatic alpha-cells the expression of Arx.

The present invention thus provides an in vitro or ex vivo method for producing a population of pancreatic beta-cells, comprising the step of inhibiting the expression or the activity of Arx in a population of pancreatic alpha-cells.

Preferably, the invention provides an in vitro or ex vivo method for producing a population of pancreatic beta-cells, comprising the step of inhibiting the expression or the activity of Arx in a population of pancreatic alpha-cells with the proviso that the inhibition of the expression of Arx is not obtained by contacting the population of pancreatic beta-cells with a Pax-4 polypeptide or a nucleic acid encoding Pax-4 gene or a vector comprising thereof.

Methods for providing at least a population of alpha-cells are known in the art and include isolating pancreatic tissue and isolating the cells, e.g. with the help of FACS (cell sorter) as known in the art or providing an alpha-cell-line (Powers, 1990). Preferably, the population of pancreatic alpha-cells is in purified form.

In one embodiment, the pancreatic alpha-cells are adult pancreatic alpha-cells.

Method for determining whether a cell has a pancreatic beta-cell phenotype are known in the art and include incubating the cell with glucose and testing whether insulin expression in the cell is increased or induced (Nolan, 2009). Other methods include the testing whether beta-cell specific transcription factors are expressed, the detection of beta-cell specific gene products with the help of RNA quantitative PCR, the transplantation of a candidate cell in diabetic mice, and subsequent testing of the physiologic response following said transplantation as well analyzing the cells with electron microscopy.

In a particular embodiment, the method comprises the followings steps consisting of isolating a population of pancreatic alpha-cells; inhibiting the expression or activity of Arx in said population of pancreatic alpha-cells; culturing said population of cells wherein the expression or activity of Arx has been inhibited in conditions allowing the α-to-β-cell conversion. Typically, said population of pancreatic alpha-cells is cultured in a liquid medium suitable for the in vitro or ex vivo culture of mammalian cells, in particular human cells. A culture medium of the invention may be based on a commercially available medium such as RPMI1640 from Invitrogen.

Inhibition of the Expression or the Activity of Arx may be Achieved by any Technique In a particular embodiment, the expression of Arx may be inhibited by using siRNA oligonucleotide, antisense oligonucleotide or ribozyme.

Anti-sense oligonucleotides, including anti-sense RNA molecules and anti-sense DNA molecules, would act to directly block the translation of Arx mRNA by binding thereto and thus preventing protein translation or increasing mRNA degradation, thus decreasing the level of Arx proteins, and thus activity, in a cell. For example, antisense oligonucleotides of at least about 15 bases and complementary to unique regions of the mRNA transcript sequence encoding for Arx may be synthesized, e.g., by conventional phosphodiester techniques. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Examples of said antisense oligonucleotides against Arx include, but are not limited to, those purchased by Qiagen.

Small inhibitory RNAs (siRNAs) can also function as inhibitors of expression of cArx for use in the present invention. Arx gene expression can be reduced by contacting pancreatic alpha-cells with a small double stranded RNA (dsRNA), or a vector or construct causing the production of a small double stranded RNA, such that expression of Arx is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836). Examples of said siRNAs against Arx include, but are not limited to, those purchased by Qiagen (FLEXITUBE GENESOLUTION® GS170302).

Ribozymes can also function as inhibitors of expression of Arx for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of Arx mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Antisense oligonucleotides, siRNA oligonucleotides and ribozymes useful as inhibitors of expression of Arx can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone. Antisense oligonucleotides, siRNA oligonucleotides and ribozymes of the invention may be delivered alone or in association with a vector. In its broadest sense, a "vector" is any vehicle capable of facilitating the transfer of the antisense oligonucleotide, siRNA oligonucleotide or ribozyme nucleic acid to pancreatic alpha-cells. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA oligonucleotide or ribozyme nucleic acid sequences.

Methods for delivering siRNAs, ribozymes and/or antisense oligonucleotides into pancreatic alpha-cells are well known in the art and include but are not limited to transfection, electroporation, microinjection, lipofection, calcium phosphate mediated transfection or infection with a viral vector containing the gene sequences, cell fusion, chromosome-mediated gene transfer, microcell-mediated gene transfer, spheroplast fusion, etc. Numerous techniques are known in the art for the introduction of foreign genes into cells and may be used in accordance with the present invention, provided that the necessary developmental and physiological functions of the recipient cells are not disrupted. The technique may provide for the stable transfer of the gene to the cell, so that the gene is expressible by the cell, heritable and expressible by its cell progeny. Usually, the method of transfer includes the transfer of a selectable marker to the cells. The cells are then placed under selection to isolate those cells that have taken up and are expressing the transferred gene. Those cells are then delivered to a subject. A variation of the technique may provide for transient transfer of oligonucleotides or oligonucleotide coding genes to pancreatic alpha-cells to enable temporary expansion of pancreatic alpha-cells ex vivo or in vivo without permanent genetic modification.

In another embodiment, the expression of Arx may be inhibited by Gamma-Amino Butyric Acid (GABA), and/or a GABA analogue, and/or a GABA receptor agonist (or partial agonist), and/or a GABA potentiator, and/or a GABA prodrug.

In one particular embodiment the GABA receptor agonist acts on both $GABA_A$ and $GABA_B$ receptors. In one particular embodiment, the GABA receptor agonist acts preferentially, or exclusively, on the $GABA_A$ or $GABA_B$ receptor.

GABA receptor agonists are well known to those of skill in the art.

Illustrative GABA receptor agonists include, but are not limited to, certain barbiturates (e.g., thiopental, thiamylal, pentobarbital, secobarbital, hexobarbital, butobarbital, amobarbital, barbital, mephobarbital, phenobarbital, primidone, and the like), certain benzodiazepines (e.g., midazolam, triazolam, lometazepam, flutazolam, nitrazepam, fluritrazepam, nimetazepam, diazepam, medazepam, oxazolam, prazeam, tofisopam, rilmazafonoe, lorazepam, temazepam, oxazepam, fluidazepam, chlordiazepoxide, cloxazolam, flutoprazepam, alprazolam, estazolam, bromazepam, flurazepam, clorazepate potassium, haloxazolam, ethyl loflazepate, qazepam, clonazepam, mexazolam, and the like), certain thienodiazepiens (e.g., etizolam, brotizolam, clotizaepam, and the like), certain dialkylphenols (e.g., propofol, fospropofol, and the like), certain non-benzodiazepines (e.g., Zolpidem, zopiclone, exzopiclone, etc.), and the like.

In another embodiment, the GABA receptor agonist is selected from the group consisting of muscimol, THIP/gaboxadol, isoguvacine, kojic amine, homotaurine, homohypotaurine, trans-aminocyclopentane-3-carboxylic acid, trans-amino-4-crotonic acid, β-guanidinopropionic acid, homo-P-proline, isonipecotic acid, 3-((aminoiminomethyl)thio)-2-propenoic acid (ZAPA), imidazoleacetic acid, and piperidine-4-sulfonic acid (P4S).

Alternatively, glutamate decarboxylase or glutamic acid decarboxylase (GAD) which is enzymes that catalyzes the decarboxylation of glutamate to GABA and $CO_2$ may be used.

In one embodiment, the GABA-synthesizing enzymes GAD65 or GAD67 are used.

Methods for contacting a population of cells, in particular a population of pancreatic alpha-cells, with a polypeptide of interest such as a GAD65 polypeptide or a GAD67 polypeptide or a vector encoding GAD65 or GAD67 gene are well known in the art.

In a further embodiment, the expression of Arx may be inhibited by compounds acting on promoter activity, RNA processing or protein stability.

In another embodiment, inhibition of the activity of Arx may be achieved by using mutated Arx polypeptides which compete with the wild-type Arx.

This technique is generally referred to as the technique of "dominant negative mutants". A dominant negative mutant is a polypeptide or a nucleic acid coding region sequence which has been changed with regard to at least one position in the sequence, relative to the corresponding wild type native version at a position which changes an amino acid residue position at an active site required for biological activity of the native peptide. For example, a dominant negative mutant may consist of a truncated Arx molecule devoid of N-terminal effector domains that may act as a competitive inhibitor of Arx for DNA binding and transactivation. The efficiency of Arx repression may be further improved by fusion to repressor domains that increase inhibitory function.

The methods of the invention are accomplished by exposing pancreatic alpha-cells to a dominant negative mutant in vitro or ex vivo. Exposure may be mediated by transfecting the cell with a polynucleotide encoding the dominant negative mutant polypeptide and expressing said dominant negative mutant encoded by the polynucleotide so that Arx activity is inhibited. Methods for transfecting such polynucleotides may consist in those above described.

Exposure may also be mediated by exposing pancreatic alpha-cells to a dominant negative mutant polypeptide directly, for instance by contacting the cell with said polypeptide preferably coupled to an internalization moiety.

Suitable internalization moieties are known in the art, and for instance may be selected from the group consisting of a peptide internalization sequence derived from proteins such as TAT polypeptide of HIV or Antennapedia or other homeoproteins. Alternatively transfer may be mediated by a liposome, and an antibody or an antibody fragment or ligand that binds to a surface receptor on the target cell.

As an alternative, inhibitors of activity may consist in molecules which are inhibitors of enzymatic posttranslational modification that regulate activity such as phosphorylation, acetylation, methylation, ribosylation, ubiquitination, small ubiqutin like molecule modification (SUMOylation, neddylation, etc.) or molecules that alter conformation or interaction with co-activators or co-repressors. As a further alternative, inhibitors of activity may consist in inhibitors of DNA binding, dimerization or co-factor interaction.

Inhibitors of activity may include macromolecules or small organic molecules. The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

In a particular embodiment, the method further comprises a step of contacting the population of pancreatic alpha-cells with a Pax4 polypeptide, a nucleic acid encoding Pax4 gene or a vector comprising thereof. Said step may be carried simultaneously or sequentially (i.e. before or after) the step of inhibiting the expression or the activity of Arx in a population of pancreatic alpha-cells, such as an antisense oligonucleotide or a siRNA against Arx, GABA or a GABA receptor agonist.

Methods for contacting a population of cells, in particular a population of pancreatic alpha-cells, with a Pax-4 polypeptide, a nucleic acid encoding Pax-4 gene or a vector comprising thereof are disclosed in the international patent application WO 2011/012707 and in Collombat et al. 2009.

Arx Deficient Cells

The methods of the invention lead to the generation of pancreatic beta-cells of great interest in the therapeutic field as well as in the screening field.

Accordingly, a second aspect of the present invention is thus a population of pancreatic beta-cells obtainable by the method as above described. Preferably, the population of pancreatic beta-cells is in purified form.

Another aspect of the present invention is a population of pancreatic alpha-cells, which does not express Arx or in which the expression or activity of Arx is abolished or inhibited. Preferably the pancreatic alpha-cells lack the Arx gene. The pancreatic alpha-cells may be of any species. It is preferably from a murine origin, or from a human origin.

In one embodiment, the pancreatic alpha-cells are adult pancreatic alpha-cells.

According to the present invention, pancreatic beta-cells can be easily and effectively generated in vitro or ex vivo. The ability to obtain a large number of in vitro or ex vivo pancreatic beta-cells opens new opportunities for the therapeutic field.

The present invention thus provides a pharmaceutical composition comprising pancreatic beta-cells as defined above, in combination with a pharmaceutically acceptable carrier.

Therapeutic Methods and Uses

The present invention provides methods and compositions (such as pharmaceutical compositions) for preventing or treating of diabetes.

In another aspect, the present invention relates to an inhibitor of Arx gene expression for use in the prevention or treatment of diabetes of a patient in need thereof.

Preferably, the invention relates to an inhibitor of Arx gene expression for use in the prevention or treatment of diabetes of a patient in need thereof with the proviso that said inhibitor of Arx gene expression is not a Pax-4 polypeptide or a nucleic acid encoding Pax-4 gene or a vector comprising thereof.

As used herein, the term "inhibitor of gene expression" refers to a natural or synthetic compound that has a biological effect to inhibit or significantly reduce the expression of a gene. Consequently an "inhibitor of Arx gene expression" refers to a natural or synthetic compound that has a biological effect to inhibit or significantly reduce the expression of the gene encoding for the Arx protein.

As used herein, "diabetes" refers to the broad class of disorders characterized by impaired insulin production and glucose tolerance. Diabetes includes type 1 and type 2 diabetes, gestational diabetes, prediabetes, insulin resistance, metabolic syndrome, and impaired glucose tolerance. Type 1 diabetes is also known as Insulin Dependent Diabetes Mellitus (IDDM). The terms are used interchangeably herein. Type 2 is also known as Non-Insulin-Dependent Diabetes Mellitus (NIDDM)).

As used herein, the term "a patient in need thereof" refers to an subject that has been diagnosed with type 1 diabetes, type 2 diabetes, gestational diabetes, pre-diabetes, insulin resistance, metabolic syndrome, or impaired glucose tolerance, or one that is at risk of developing any of these disorders. Patients in need of treatment also include those that have suffered an injury, disease, or surgical procedure affecting the pancreas, or individuals otherwise impaired in their ability to make insulin. Such patients may be any mammal, e.g., human, dog, cat, horse, pig, sheep, bovine, mouse, rat or rabbit (preferably a human).

The term "preventing a disorder" as used herein, is not intended as an absolute term. Instead, prevention, e.g., of type 2 diabetes, refers to delay of onset, reduced frequency of symptoms, or reduced severity of symptoms associated with the disorder. Prevention therefore refers to a broad range of prophylactic measures that will be understood by those in the art. In some circumstances, the frequency and severity of symptoms is reduced to non-pathological levels, e.g., so that the individual does not need traditional insulin replacement therapy. In some circumstances, the symptoms of a patient receiving an inhibitor of Arx gene expression according to the invention are only 90, 80, 70, 60, 50, 40, 30, 20, 10, 5 or 1% as frequent or severe as symptoms experienced by an untreated individual with the disorder.

Similarly, the term "treating a disorder" is not intended to be an absolute term. In some circumstances, the inhibitors of Arx gene expression according to the invention seek to reduce the loss of insulin producing cells that lead to diabetic symptoms. In some circumstances, treatment with the inhibitors of Arx gene expression leads to an improved prognosis or a reduction in the frequency or severity of symptoms.

In a particular embodiment, the inhibitor of Arx gene expression is a siRNA oligonucleotide, a ribozyme, or an antisense oligonucleotide as previously described.

The present invention also relates to a method for preventing or treating (e.g. prophylactic treatment) diabetes comprising administering to a patient in need thereof an inhibitor of Arx gene expression.

Inhibitors of Arx gene expression may be administered in the form of a pharmaceutical composition, as defined below. Preferably, said inhibitor is administered in a therapeutically effective amount. By a "therapeutically effective amount" is meant a sufficient amount of the inhibitor of Arx gene expression to prevent or treat diabetes at a reasonable benefit/risk ratio applicable to any medical treatment.

In a particular embodiment, the inhibitor of Arx gene expression is a siRNA oligonucleotide, a ribozyme, or an antisense oligonucleotide as previously described.

It will be understood that the total daily usage of the compounds of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

In other aspect, the present invention relates to an inhibitor of Arx gene expression for use in a method for the inducing conversion of pancreatic alpha-cells in pancreatic beta-cells in a patient in need thereof.

Preferably, the present invention relates to an inhibitor of Arx gene expression for use in a method for the inducing conversion of pancreatic alpha-cells in pancreatic beta-cells in a patient in need thereof with the proviso that said inhibitor of Arx gene expression is not a Pax-4 polypeptide or a nucleic acid encoding Pax-4 gene or a vector comprising thereof.

The present invention also relates to a method for inducing the conversion of pancreatic alpha-cells in pancreatic beta-cells in a patient in need thereof, comprising administering to said patient in need thereof a therapeutically effective amount of an inhibitor of Arx gene expression.

In one embodiment, the inhibitor of Arx gene expression is not a Pax-4 polypeptide or a nucleic acid encoding Pax-4 gene or a vector comprising thereof.

The term "conversion" is used interchangeably herein with the phrase "transdifferentiation" and refers to the conversion of one differentiated somatic cell type into a different differentiated somatic cell type without undergoing complete reprogramming to an induced pluripotent stem cell (iPSC) intermediate. Preferably, promoting conversion of a somatic cell, e.g., pancreatic alpha-cells into pancreatic beta-cells as disclosed herein will result in greater than about 5% or about 10% of conversion of a somatic cell, e.g., pancreatic alpha-cells into pancreatic beta-cells. Even more preferably, greater than about 25%, 30%, 35%, 40%, 45%, 50%, 55%, 60%, 65%, 70%, 75%, 80%, 85%, or 90% of the a somatic cell, e.g., pancreatic alpha-cells will be converted into pancreatic beta-cells.

In one embodiment, the inhibitor of Arx gene expression is a siRNA oligonucleotide, a ribozyme, or an antisense oligonucleotide as defined above.

In another embodiment, the inhibitor of Arx gene expression is Gamma-Amino Butyric Acid (GABA), and/or a GABA analogue, and/or a GABA receptor agonist (or partial agonist), and/or a GABA potentiator, and/or a GABA pro-drug.

In one particular embodiment the GABA receptor agonist acts at both $GABA_A$ and $GABA_B$ receptors. In one particular embodiment, the GABA receptor agonist acts preferentially, or exclusively, at the $GABA_A$ or $GABA_B$ receptor.

GABA receptor agonists are well known to those of skill in the art.

Illustrative GABA receptor agonists include, but are not limited to, certain barbiturates (e.g., thiopental, thiamylal, pentobarbital, secobarbital, hexobarbital, butobarbital, amobarbital, barbital, mephobarbital, phenobarbital, primidone, and the like), certain benzodiazepines (e.g., midazolam, triazolam, lometazepam, flutazolam, nitrazepam, fluritrazepam, nimetazepam, diazepam, medazepam, oxazolam, prazeam, tofisopam, rilmazafonoe, lorazepam, temazepam, oxazepam, fluidazepam, chlordiazepoxide, cloxazolam, flutoprazepam, alprazolam, estazolam, bromazepam, flurazepam, clorazepate potassium, haloxazolam, ethyl loflazepate, qazepam, clonazepam, mexazolam, and the like), certain thienodiazepiens (e.g., etizolam, brotizolam, clotizaepam, and the like), certain dialkylphenols (e.g., propofol, fospropofol, and the like), certain non-benzodiazepines (e.g., Zolpidem, zopiclone, exzopiclone, etc.), and the like.

In another embodiment, the GABA receptor agonist is selected from the group consisting of muscimol, THIP/gaboxadol, isoguvacine, kojic amine, homotaurine, homohypotaurine, trans-aminocyclopentane-3-carboxylic acid, trans-amino-4-crotonic acid, β-guanidinopropionic acid, homo-P-proline, isonipecotic acid, 3-((aminoiminomethyl)thio)-2-propenoic acid (ZAPA), imidazoleacetic acid, and piperidine-4-sulfonic acid (P4S).

In a particular embodiment, the inhibitor of Arx gene expression (such as a siRNA against Arx, GABA or a GABA receptor agonist) is administered at long-term.

Indeed, as described in the Examples below, mice have been treated with GABA for 2 or 3 months in order to reveal an increase in the number of insulin-expressing cells and in the number of islets. It is noted that humans are treated generally longer than the mice or other experimental animals exemplified herein which treatment has a length proportional to the length of the disease process and drug effectiveness. The doses can be single doses or multiple doses over a period of several days, preferably for a period of several weeks, or more preferably for a period of several months. By way of an example but not as a limitation, the inhibitor of Arx gene expression may be administered to a patient in need thereof at regular intervals, for example but not limited to weekly or monthly etc by any suitable means known by persons of ordinary skill in the art for several weeks or several months.

Moreover, the inhibitor of Arx gene expression may be intermittently administered to a patient in need thereof intermittently. As used herein, the term "intermittent administration" refers to a period of administration of a therapeutically effective amount of an inhibitor of Arx gene expression, followed by a time period of discontinuance, which is then followed by another period of administration of a therapeutically effective amount, and so forth. By way of an example but not as a limitation, the inhibitor of Arx gene expression may be administered to a patient in need thereof at regular intervals, for example but not limited to weekly or monthly etc by any suitable means known by persons of ordinary skill in the art for several weeks or several months, the stopped for several weeks or several months, and administered again to the patient weekly or monthly for several weeks or several months.

Pharmaceutical Compositions

The inhibitor of Arx gene expression may be combined with pharmaceutically acceptable excipients, and optionally sustained-release matrices, such as biodegradable polymers, to form therapeutic compositions.

In the pharmaceutical compositions of the present invention, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The inhibitor of Arx gene expression of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The inhibitor of Arx gene expression of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

In a particular aspect, the invention relates to a pharmaceutical composition for use in a method for the inducing conversion of pancreatic alpha-cells in pancreatic beta-cells in a patient in need thereof comprising GABA or a GABA receptor agonist as above described.

Combination Therapies of the Invention

The inhibitor of Arx gene expression of the invention may be administered to a patient with an appropriate additional therapeutic agent such as an immunosuppressive agent useful for improving survival of the newly generated pancreatic beta-cells.

The invention relates to a pharmaceutical composition or a kit-of-part composition comprising an inhibitor of Arx gene expression and an immunosuppressive agent.

The invention also relates to a method for improving the survival of regenerated pancreatic beta-cells in a patient in need thereof comprising a step of administering to said patient a therapeutically effective amount of inhibitor of Arx gene expression and a therapeutically effective amount of an immunosuppressive agent.

In one embodiment, the inhibitor of Arx gene expression is a siRNA oligonucleotide, a ribozyme, or an antisense oligonucleotide as defined above.

In another embodiment, the inhibitor of Arx gene expression is GABA or a GABA receptor agonist as defined above.

Immunosuppressive agents are drugs that inhibit or prevent activity of the immune system and are well known for the skilled man in the art.

In one embodiment, the immunosuppressive agent include, but are not limited to, one or more compounds selected from the group consisting of azathioprine, mycophenolic acid, leflunomide, teriflunomide, methotrexate, FKBP/cyclophilin, tacrolimus, ciclosporin, pimecrolimus, abetimus, gusperimus, sirolimus, deforolimus and everolimus.

The term "combination therapy" or "in combination with" as used herein means two or more substances, for example GABA and Ciclosporin or GABA and Sirolimus, are administered to a subject over a period of time, contemporaneously or sequentially e.g. the substances are administered at the same time or at different times within the period of time in a regimen that will provide beneficial effects of the drug combination, at similar or different intervals. For example, the combination therapy is intended to embrace co-administration, in a substantially simultaneous manner such as in a single dosage form e.g. a capsule, having a fixed ratio of active ingredients or in multiple, separate dosage forms, e.g. capsules, for each substance. The compounds may or may not be biologically active in the subject at the same time. As an example, a first substance is administered weekly, and a second substance administered daily. The exact details of the administration will depend on the pharmacokinetics of the two substances. Designs of suitable dosing regimens are routine for one skilled in the art.

Accordingly, in another aspect, the invention relates to a pharmaceutical composition comprising an inhibitor of Arx gene expression and an immunosuppressive agent for use in improving the survival of regenerated pancreatic beta-cells in a patient in need thereof.

In one embodiment, the inhibitor of Arx gene expression is a siRNA oligonucleotide, a ribozyme, or an antisense oligonucleotide as defined above.

In another embodiment, the inhibitor of Arx gene expression is GABA or a GABA receptor agonist as defined above.

In another aspect, the invention relates to a kit-of-part composition comprising comprising an inhibitor of Arx gene expression and an immunosuppressive agent for use in improving the survival of regenerated pancreatic beta-cells in a patient in need thereof.

In one embodiment, the inhibitor of Arx gene expression is a siRNA oligonucleotide, a ribozyme, or an antisense oligonucleotide as defined above.

In another embodiment, the inhibitor of Arx gene expression is GABA or a GABA receptor agonist as defined above.

The terms "kit", "product" or "combined preparation", as used herein, define especially a "kit-of-parts" in the sense that the combination partners as defined above can be dosed independently or by use of different fixed combinations with distinguished amounts of the combination partners, i.e. simultaneously or at different time points. The parts of the kit of parts can then, e.g., be administered simultaneously or chronologically staggered, that is at different time points and with equal or different time intervals for any part of the kit of parts. The ratio of the total amounts of the combination partners to be administered in the combined preparation can be varied. The combination partners can be administered by the same route or by different routes. When the administration is sequential, the first partner may be for instance administered 1, 2, 3, 4, 5, 6, 12, 18 or 24 h before the second partner.

Screening Methods

As previously mentioned, the methods of the invention lead to the generation of pancreatic beta-cells of great interest in the screening field.

Accordingly, another aspect of the present invention relates to a method for the screening of a pancreatic-beta-cell phenotype-inducing compound, comprising the steps of a) contacting at least one cell with a given compound, and b) testing whether said compound is capable of inhibiting Arx gene expression.

In a particular embodiment, said cell is a pancreatic alpha-cell.

Alternatively, other adult cells, especially liver cells, duct cells or intestinal cells can be used as the starting material of the method of the present invention.

As a further alternative, every precursor cell being capable of differentiating into pancreatic beta-cells can be used as the starting cell of the method of the invention. In a particular embodiment, said precursor cell is selected from the group consisting of a pancreatic precursor cell, a small intestine precursor cell, a liver precursor cell, a precursor cell derived from the duct population, and a pancreatic stem cell.

In another particular embodiment, said testing includes determining whether after the contacting the cell is also capable of producing insulin, in particular after incubation of the cells with glucose. This readout of the screening of the invention is especially suitable because the capacity of producing insulin is the major feature of pancreatic beta-cells.

It results that said testing includes both the capacity of producing insulin as well determining the expression of Arx.

Thus, in a preferred embodiment, the method for screening a compound useful for inducing pancreatic-beta-cell phenotype comprising the steps of: (a) selecting a test compound that inhibits the expression of Arx by performing a method as described above (b) determining whether said compound induces the production of insulin in a cell and (c) positively selecting the test compound capable of inducing the production of insulin in a cell.

Methods for Determining the Expression Level of a Gene

Determination of the expression level of a gene can be performed by a variety of techniques well known in the art.

Generally, the expression level as determined is a relative expression level. For example, the determination comprises contacting the biological sample (e.g. a cell sample contacted with a test compound) with selective reagents such as probes, primers or ligands, and thereby detecting the presence, or measuring the amount, of polypeptide or nucleic acids of interest originally in said biological sample. Contacting may be performed in any suitable device, such as a plate, microtiter dish, test tube, well, glass, column, and so forth. In specific embodiments, the contacting is performed on a substrate coated with the reagent, such as a nucleic acid array or a specific ligand array. The substrate may be a solid or semi-solid substrate such as any suitable support comprising glass, plastic, nylon, paper, metal, polymers and the like. The substrate may be of various forms and sizes, such as a slide, a membrane, a bead, a column, a gel, etc. The contacting may be made under any condition suitable for a detectable complex, such as a nucleic acid hybrid or an antibody-antigen complex, to be formed between the reagent and the nucleic acids or polypeptides of the biological sample.

As used herein, the term "determining" includes qualitative and/or quantitative detection (i.e. detecting and/or measuring the expression level) with or without reference to a control or a predetermined value. As used herein, "detecting" means determining if Arx is present or not in a biological sample and "measuring" means determining the amount of Arx in a biological sample. Typically the expression level may be determined for example by RT-PCR or immunohistochemistry (IHC) performed on a biological sample.

In a particular embodiment, the expression level may be determined by determining the quantity of mRNA.

Methods for determining the quantity of mRNA are well known in the art. For example the nucleic acid contained in the biological samples (e.g., cell or tissue prepared from the patient) is first extracted according to standard methods, for example using lytic enzymes or chemical solutions or extracted by nucleic-acid-binding resins following the manufacturer's instructions. The extracted mRNA is then detected by hybridization (e.g., Northern blot analysis) and/or amplification (e.g., RT-PCR). Quantitative or semi-quantitative RT-PCR is preferred. Real-time quantitative or semi-quantitative RT-PCR is particularly advantageous.

Other methods of Amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more preferably 85% identical and even more preferably 90-95% identical.

Other methods for determining the expression level of said genes include the determination of the quantity of proteins encoded by Arx gene.

Such methods comprise contacting the sample with a binding partner capable of selectively interacting with a marker protein present in the sample. The binding partner is generally an antibody that may be polyclonal or monoclonal, preferably monoclonal. Monoclonal antibodies directed against Arx are well known from the skilled man in the art such as the antibodies commercialized by Abcam (anti-Arx antibody ab48856).

Test Compounds of the Invention

According to one embodiment of the invention, the test compound of may be selected from the group consisting of peptides, proteins, peptidomimetics, small organic molecules, aptamers or nucleic acids. For example, the test compound according to the invention may be selected from a library of compounds previously synthesised, or a library of compounds for which the structure is determined in a database, or from a library of compounds that have been synthesised de novo. In a particular embodiment, the test compound may be selected from small organic molecules as above-defined.

In one embodiment, the test compound is a compound known as a GABA analogue, a GABA receptor agonist (or partial agonist), a GABA potentiator or a GABA prodrug.

The invention will be further illustrated by the following figures and examples. However, these examples and figures should not be interpreted in any way as limiting the scope of the present invention.

FIGURES

FIG. 1: Quantification of endocrine cells in Glu-ArxKO and IndGlu-ArxKO pancreata. Quantitative comparison of the numbers of insulin- (A), glucagon- (B) and somatostatin- (C) expressing cells between 6 month-old Glu-ArxKO, 4mDox+ IndGlu-ArxKO and age-matched WT mice. A significant increase in the numbers of insulin- and somatostatin-expressing cells was observed in both transgenic lines compared to controls, while variations were noted in the number of glucagonexpressing cells. n=3, ** $p<0.01$ using ANOVA.

FIG. 2: The insulin$^+$ cells generated upon Arx inactivation are functional. 2.5 month-old Glu-ArxKO (and age/sex-matched controls) were challenged with glucose (A). Mutant animals displayed an increased capacity to counteract the glucose bolus with a lower peak in glycemia and a faster return to euglycemia, suggestive of an increased β-cell mass, further indicated by the augmented levels of circulating insulin in Glu-ArxKO animals compared to their WT counterparts (Table inserted in A). Similar results were also evident in 1.2mDox+ IndGlu-ArxKO animals (B and Table inserted), where a faster reduction in glucose levels and return to euglycemia were observed compared to both WT and Dox-controls (B). The challenge of both transgenic lines with insulin resulted in no significant difference compared to their control counterparts (C-D), indicating that insulin remains fully active despite the β-like cell hyperplasia. IndGlu-ArxKO animals were subsequently subjected to streptozotocin treatment after 1.5 months (E) or, only 0-10 days (F) following Dox treatment initiation. In both cases, by the monitoring of glycemic levels, following an initial peak in glycemia, a steady recovery was noted in the induced animals, while controls either maintained their hyperglycemic state or succumbed to excessive glycemic levels. n>6 for all experiments *** $p<0.001$, * $p<0.05$ using ANOVA.

Figure 3:
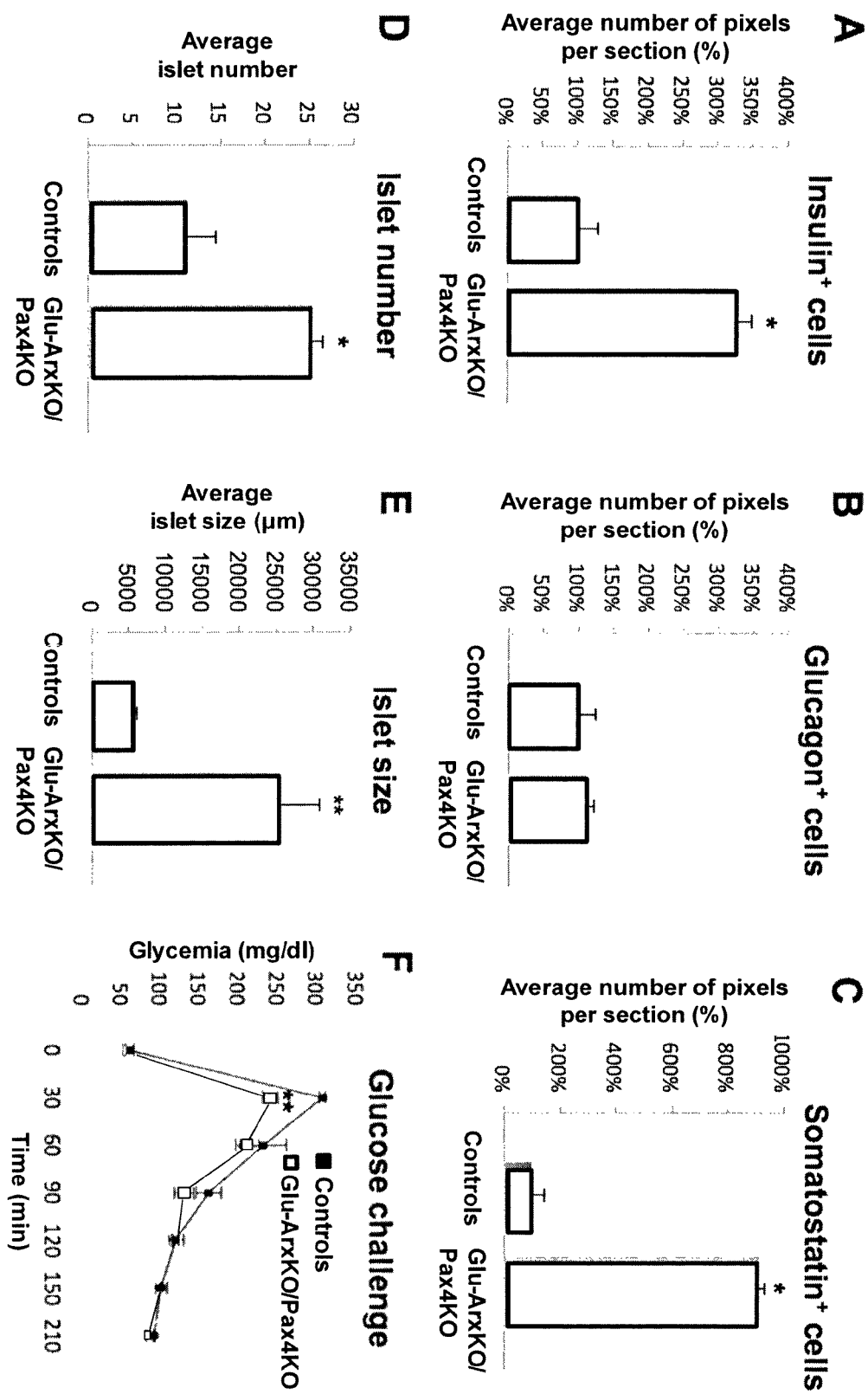

FIG. 3: Quantitative analyses upon the dual inactivation of Arx and Pax4 in glucagon-producing cells. (A-E) Quantitative comparison of the number of insulin- (A), glucagon- (B) and somatostatin- (C) expressing cells between 5 month-old Glu-ArxKO/Pax4KO animals and age-/sex-matched WT controls. A significant increase in the numbers of insulin- and somatostatin-expressing cells was observed in Glu-ArxKO/Pax4KO animals, whilst no significant variation in glucagon$^+$ cells was noted. Interestingly, both islet count (D) and size (E) were significantly increased in these animals compared to their WT counterparts, suggesting a process of islet neogenesis in addition to an increased insulin$^+$ cell mass. (F) 3 month-old Glu-ArxKO/Pax4KO animals (and age/sex-matched WT controls) were challenged with glucose. Doublemutant animals displayed an increased capacity to counteract the glucose bolus with a lower peak in glycemia, suggestive of a functional increased β-cell mass. n≤3 in all experiments, ** $p<0.01$, * $p<0.05$ using ANOVA.

Figure 4:
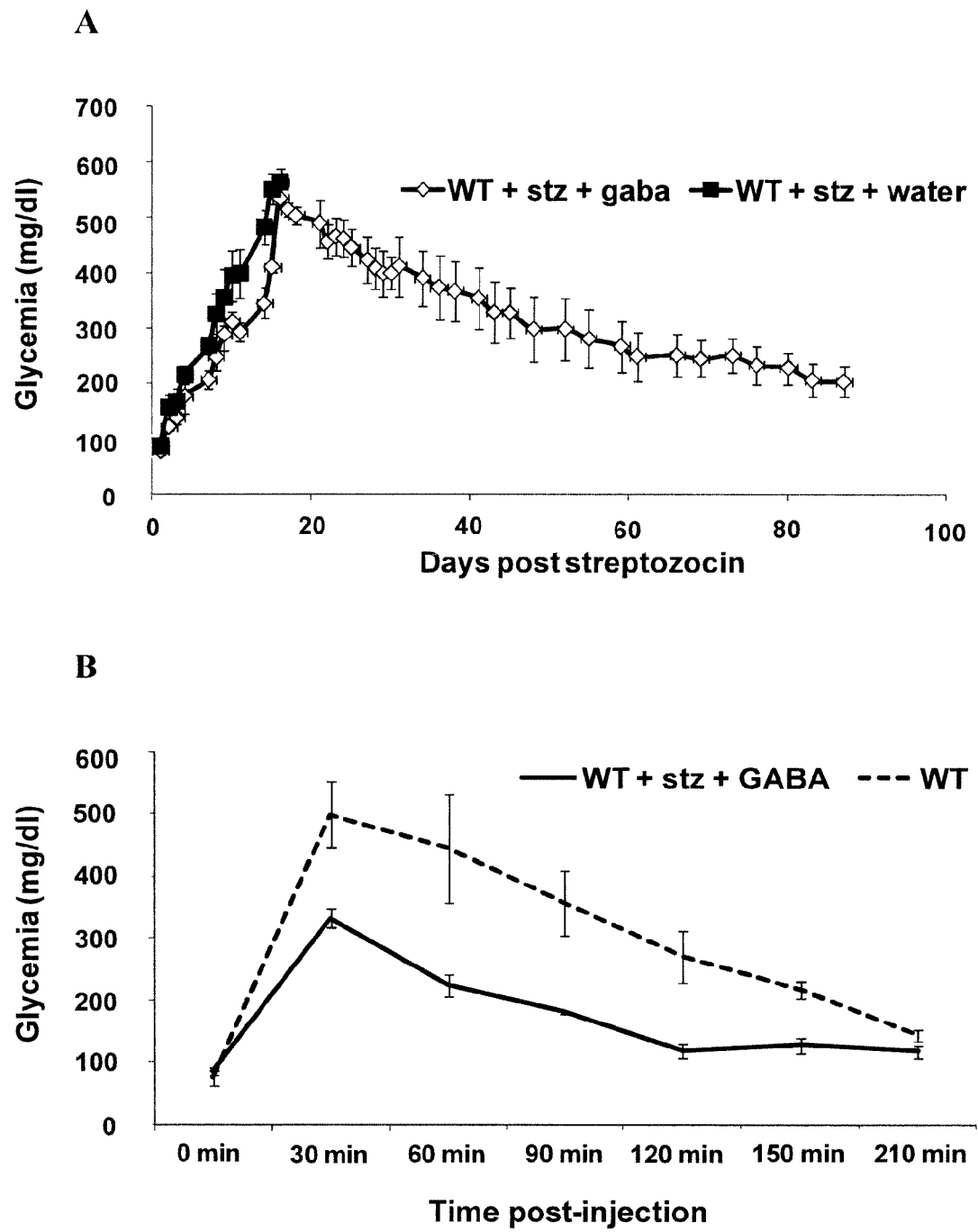

FIG. 4: The β-like cell mass can be regenerated following streptozotocin treatment in GABA-treated mice, the neo-generated insulin$^+$ cells being functional. WT mice were subjected to streptozotocin (STZ) treatment and 15 to 20 days after, they were treated with GABA or water. Following a peak in glycemia, a steady recovery is noted for GABA-treated animals while controls die from extreme hyperglycemia (A). Such a recovery is associated with a clear regeneration of their β-cell mass monitored 5, 10, 25 and 45 days post-streptozotocin administration by immunochemistry. 85 days post-streptozotocin injection, GABA- and STZ-treated WT and non-treated controls were subjected to a glucose tolerance test (GTT) (B). GABA-treated mice performed better than controls with a lower peak in glycemia and a faster return to euglycemia, suggestive of an increased β-cell mass.

Figure 5:
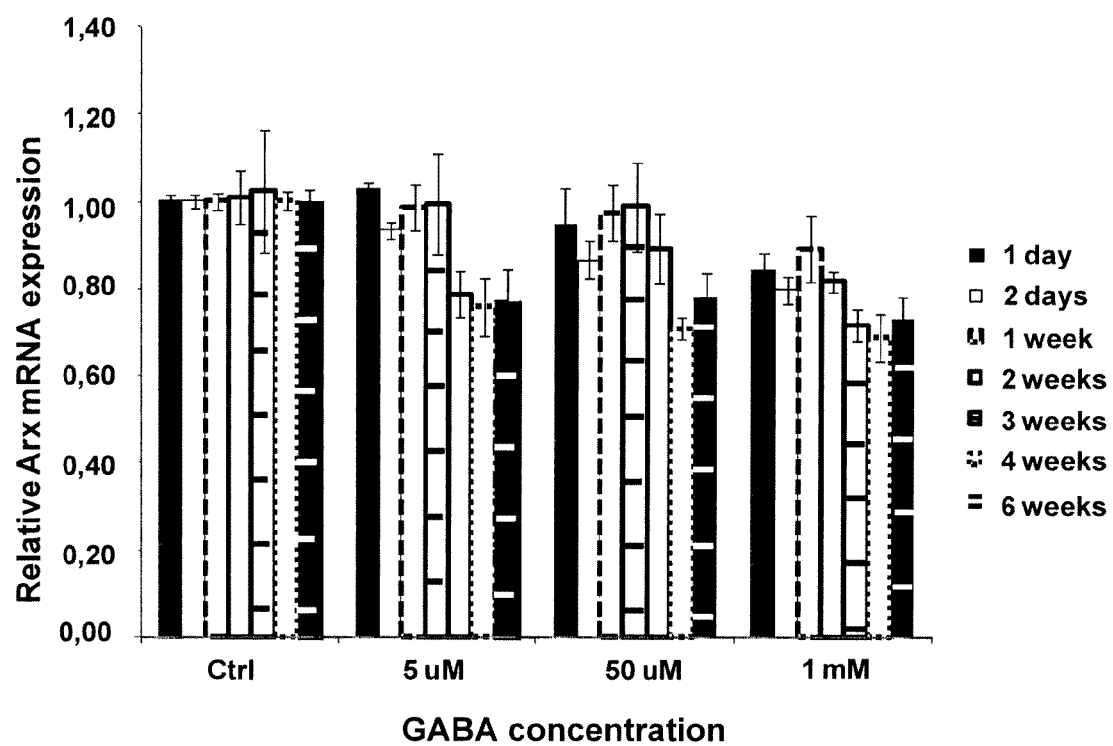

FIG. 5: Relative Arx mRNA expression in a-TC1-6 cells treated with GABA: α-TC1-6 cells were treated with increasing GABA concentrations for different periods of time. Relative Arx mRNA expression was measured in the different conditions. A decrease in Arx expression was observed in the cells treated with GABA compared to non-treated cells. * $p<0.05$,  $p<0.01$, * $p<0.001$; n≥3; data statistically analyzed by a one-way ANOVA, all data depicted as mean±SEM.

EXAMPLE 1

Genetic Inhibition of Arx Expression

Material & Methods

Mouse manipulations: To study the invalidation of the Arx gene specifically in pancreatic α cells, two transgenic lines were used. Firstly, a classical Cre-LoxP approach was used (ArxcKO::GluCre) by the crossing of the previously described ArxcKO (Fulp et al., 2008), generated by homologous recombination by inserting two loxP sites around the second exon of the Arx gene, and the classical glucagon-cre mouse line, described by Herrera et al. (2000). Linage tracing experiments were achieved by the crossing of ArxcKO animals with a GluCre-ROSA26-β-Gal mouse line (Soriano, 1999). Secondly, a inducible system was generated taking advantage of the TetOn system (Clonetech) whereby double transgenic mice obtained by the crossing of Glu-rtTA and TetOCre (Belteki et al., 2005) mice, were further crossed with ArxcKO mice and the GluCre-ROSA26-β-Gal mouse line for lineage tracing purposes. In the resulting triple transgenic mouse line (ArxcKO::Glu-rtTA-TetOCre), Arx is conditionally inactivated specifically in glucagon-expressing cells and only upon doxycycline treatment. Doxycycline (Sigma) was administered via the drinking water prepared freshly once a week at a concentration of 2 g/L. To assess the cellular proliferation upon doxycycline-mediated induction of Arx, ArxcKO::Glu-rtTA-TetOCre mice were treated with doxycycline and subsequently with BrdU for 10 days prior to examination. Cells that had incorporated BrdU during DNA replication were detected by immunohistochemistry (Invitrogen).

To analyze the inactivation of Pax4 in Arx mutants, Pax4 conditional knockout mice, previously described by Kordowich et al. 2012, were crossed with Glu-Cre::ArxcKO animals (Glu-Cre::ArxcKO::Pax4cKO).

Immunohistochemistry: Tissues were fixed in 4% PFA for 30 min at 4° C., embedded in paraffin and 8 µm sections applied to slides. These sections were assayed as described previously (Collombat et al., 2003). The primary antibodies used were the following: guinea pig polyclonal anti-insulin (1/500-Linco), anti-glucagon (1/500-Linco), mouse monoclonal anti-insulin (1/500-Sigma), anti-glucagon (1/500-Sigma), rat anti-somatostatin (1/250-Millipore), rabbit anti-PP (1/100), anti-Glut2 (1/5000), anti-PC1/3 (1/500), anti-Nkx6.1 (1/3000), anti-Pdx1 (1/1000), anti-NeuroD1 (1/200), anti-pax4 (1/4000), anti-Arx (1/500-), mouse anti-BrdU (1/40). The secondary antibodies (1/1000-Molecular Probes) used were: 594-alexa anti-mouse; 488-alexa anti-mouse; 594-alexa anti-rabbit; 488-alexa anti-rabbit; 594-alexa anti-guinea pig; 488-alexa anti-guinea pig; 488-alexa anti-rat. Pictures were processed using ZEISS Axioimager Z1 and LEICA DM 6000 B. For quantification purpose, stained cells were counted manually on every tenth section.

β-galactosidase-based lineage-tracing experiments: Pancreatic tissues were isolated and fixed for 30 min at 4° C. in a solution containing 1% formaldehyde, 0.2% glutaraldehyde, 0.02% NP40. The tissues were dehydrated in 25% sucrose overnight at 4° C. Prior to sectioning, tissues were embedded in freezing medium. For β-galactosidase activity assessment, the tissues were washed in PBS and then incubated overnight in staining solution (500 mM $K_3Fe(CN)_6$, 250 mM $K_4Fe(CN)_6$, 0.5M $MgCl_2$, 40 mg/ml X-gal in DMF).

Challenges and blood glucose levels measurement: For challenge purposes, animals were fasted for 16 h and injected intraperitoneally with glucose (2 g/kg of body-weight) or insulin (0.75 U/kg). Blood glucose levels were measured at the indicated time points post-injection with a ONETOUCH Vita glucometer (Life Scan, Inc., CA).

Electron microscopy: For ultrastructural analyses, anesthetized mice were perfused transcardially with physiological serum, then with 2% glutaraldehyde in 0.1 M cacodylate buffer. Pancreas were dissected, immerged in fixative for hours, post-fixed for 2 h in 1% osmium tetroxide in 0.1 M cacodylate buffer and embedded in epoxy resin. Contrasted ultrathin sections (70 nm) were analyzed under a JEOL 1400 transmission electron microscope mounted with a Morada Olympus CCD camera.

For immuno-gold staining, 200 islets, isolated by collagenase (1 mg/ml) digestion, were fixed with 4% paraformaldehyde, 0.2% glutaraldehyde in 0.1 M phosphate buffer (PB) (pH 7.4) overnight at 4° C. and were processed for ultracryomicrotomy according to a slightly modified Tokuyasu method (Tokuyasu KT 1973). Immunostainings were processed with an automated immuno-gold labeling system Leica EM IGL using guinea-pig anti-insulin primary antibody (1/500) and 15 nm colloidal gold conjugated protein AG (CMC, University Medical Center, Utrecht, The Netherlands). Sections were examined under a JEOL 1400 transmission electron microscope.

Optical projection tomography, volumetric quantification and image analysis: OPT analysis was performed as previously described (Sand et al., 2012). Each specimen was scanned using the Bioptonics 3001 OPT scanner with a resolution of 1024×1024 pixels and reconstructed with the NRecon version 1.6.1.0 (Skyscan) software.

Quantification of the insulin-producing cell mass was undertaken using Imaris software (Biplane). Volumes were calculated by applying a "find objects by intensity" task to select voxels above a specified intensity. The intensity threshold value was manually determined for each image stack. All pancreata was scanned and analyzed blinded.

Induction of streptozotocin-mediated diabetes: To induce hyperglycaemia, STZ (Sigma) was dissolved in 0.1M sodium citrate buffer (pH 4.5), and a single dose was administered intraperitoneally (100 mg/kg) within 10 min of dissolution. Diabetes was assessed by monitoring the blood glucose levels and/or survival rates of mice.

Data Analysis: All values are depicted as mean±SEM and considered significant if $P<0.05$. Data were statistically analyzed by ANOVA.

RNA Analysis: RNA was isolated (RNEASY® (RNA isolation kit), Qiagen) and cDNA synthesis (SUPERSCRIPT® (cDNA synthesis kit) choice system, Invitrogen) was performed according to the manufacturer's instructions. Quantitative RT-PCR was carried out using validated primers (Qiagen) and the QUANTITECT® SYBR Green RT-PCR Kit (Qiagen) following manufacturer's instructions. PCR reactions and detection were performed on a MASTERCYCLER® ep realplex cycler using GAPDH and HPRT1 as internal controls for normalization purposes.

Results

The Inactivation of Arx at any age results in insulin-producing cell hyperplasia: To determine the consequences of the loss of Arx in α-cells, we first generated animals allowing the constitutive deletion of Arx in all glucagon-producing cells by crossing the ArxcKO mouse line (in which the second exon of the Arx gene is flanked by LoxP sites as described [Fulp et al., 2008]) with Glu-Cre transgenic animals (generated using a transgene composed of the glucagon promoter driving the expression of the phage P1 Cre recombinase). The resulting double transgenics (referred to as Glu-ArxKO) were further crossed with ROSA26-LoxP-Neomycin Resistance-STOP-LoxP-β-gal animals (containing a transgene encompassing the ubiquitous ROSA26 promoter in front of a fusion of the neomycin resistance gene with STOP codons flanked by LoxP sites and followed by the β-galactosidase cDNA [Soriano, 1999]—henceforth referred to as Rosa) for lineage tracing purposes.

Several tests were performed to determine the efficiency of this approach. First, by combining several immunohistochemical approaches, we analyzed 2 week-old homozygous Glu-Cre::Rosa animals to further verify the efficiency of glucagon mediated Cre activity. Our results demonstrated approximately 72±7% of glucagon$^+$ β-gal$^+$ cells in the pancreas of these animals, a result in line with previously published data [Collombat et al., 2009, Herrera, 2000, Quoix et al., 2007]. Next, aged-matched Glu-ArxKO pancreata were assayed for Arx expression: quantitative analyses indicated a loss of Arx expression in approximately 70±6% of glucagon-producing cells as compared to ArxKO or wild-type controls, a proportion matching the content of Cre$^+$ cells. Of note, in a number of these Arx$^-$ Glucagon$^+$ cells, Pax4 was clearly detected, suggesting that the loss of Arx can induce the ectopic expression of Pax4 in α-cells. Lastly, qPCR was used to quantify the Arx transcript content: a comparison of controls versus Glu-ArxKO pancreata outlined a 74% reduction in Arx transcripts upon Arx deficiency, a result in line with cell quantification. Taken together, our results suggest that, in this experimental model, Cre can efficiently lead to the inactivation of Arx in glucagon-producing cells.

In a second set of experiments, to develop an animal model permitting the inducible deletion of Arx in adult α-cells, the ArxcKO mouse line was crossed with the Glu-rtTA transgenic line (containing a transgene composed of the rat glucagon promoter [Herrera et al., 1994] upstream of the reverse tetracycline-dependent transactivator) and further mated with TetO-Cre animals (whose transgene includes the Tet operator upstream of Cre Recombinase cDNA [Perl et al., 2009]). The resulting triple transgenic mice will henceforth be referred to as IndGlu-ArxKO (inducible Glu-ArxKO). To assess the specificity of the regulatory sequences and any putative leakiness of transgene expression, Glu-rtTA mice were initially crossed with the well established TetO-β-gal mouse line [Henninghausen et al., 1995]. Pancreata of 6 week-old Glu-rtTA::TetO-β-gal mice were assayed for β-galactosidase expression in glucagon$^+$ cells following 2 weeks of doxycycline (Dox) treatment. From hereon, mice treated with Doxycycline for x months will be referred to as xmDox+. In all cases, untreated animals were found phenotypically similar to their wild-type (WT) counterparts, they will be referred to as "Dox−" or "controls". Transgene expression was found specifically regulated by Glu-rtTA as β-galactosidase activity was detected in approximately 80 to 90% of glucagon$^+$ cells but not in any other cell subtype of the pancreas. The combined analysis of Arx-, glucagon-, and Pax4-producing cells outlined a loss of Arx in approximately 89±9% of glucagon-labeled cells, few of which initiated Pax4 expression, indicating that, in this inducible model, Arx can be efficiently inactivated in glucagon-producing cells.

Both Glu-ArxKO and Dox+ IndGlu-ArxKO were found viable and fertile, their life expectancy or basal glycemia remaining within normal range (Table S1-2). Interestingly, a substantial increase in islet size was noted in both animal models (Table S1-2). Further analyses indicated that a large insulin$^+$ cell hyperplasia was the reason underlying the observed islet hypertrophy. In Glu-ArxKO animals, a correlation between age and islet overgrowth was apparent, albeit a plateau phase was observed following 4 months of age (Table S1). Similarly, in Dox+ IndGlu-ArxKO, the degree of islet hyperplasia was found to depend on the duration of Dox treatment rather than on the age of Dox induction (Table S2). As important was the finding that, in both cases, a dramatic increase in islet number was apparent, suggestive of islet neogenesis (Table S1-2). The increased number of islets and the insulin+ cell hyperplasia were further demonstrated by means of optical projection tomography allowing the examination of insulin+ cells in the entire pancreas. Indeed, a global pancreatic increase of 171±9% in the number of insulin+ cells was thereby outlined in 5 month-old Glu-ArxKO pancreata as compared to age-matched controls. Together, our data suggest that the inactivation of Arx in α-cells of any age results in a clear islet hypertrophy caused by an insulin+ cell hyperplasia and a substantial increase in islet number.

TABLE S1

Assessment of the life expectancy, glycemic levels, islet size, and islet number in Glu-ArxKO animals. Glu-ArxKO mice were examined at the indicated ages. Life expectancy and basal glycemia (monitored weekly) were found within normal ranges, as compared to controls. Glu-ArxKO animals displayed a clear increase in islet size dependent on age, however this increase appeared to plateau at approximately 4 months of age. An increase in the islet number was also observed, suggestive of islet neogenesis, which peaked at an average of x1.98 compared to controls.

Glu-ArxKO animals

| Age of examination | Life expectancy | Basal glycaemia | Islet count versus age-/sex-matched controls | Islet size versus age-/sex-matched controls |
|---|---|---|---|---|
| 2.4 months | Normal | 167 | x 1.4 | x 1.8 |
| 4 months | Normal | 121 | x 1.7 | x 3.3 |
| 6.1 months | Normal | 172 | x 2.6 | x 3.4 |
| 7.2 months | Normal | 141 | x 2.1 | x 3.3 |
| 11.4 months | Normal | 140 | x 2.1 | x 3 |

TABLE S2

Assessment of the life expectancy, glycemic levels, islet size, and islet number in IndGlu-ArxKO animals. The IndGlu-ArxKO mice were treated with Dox at different ages and were examined after the indicated lengths of Dox treatment (values sorted based on Dox treatment duration). Life expectancy and basal glycemia (monitored weekly) were found within normal ranges, as compared to controls, in all conditions analyzed. Interestingly, a near doubling (1.8x) in islet size was observed after just 14 days of Dox with a steady increase in islet size dependent on length of Dox treatment until a plateau appeared to be reached after approximately 4 months of Dox treatment. No large variations were observed in islet number between the different durations of Dox treatment however, on average, a 1.9-fold increase was observed in Dox+ IndGlu-Arx animals compared to age-matched controls.

Dox+ IndGlu-ArxKO animals

| Dox Treatment Age | Dox Treatment Duration | Life expectancy | Basal glycaemia | Islet count versus age-/sex-matched controls | Islet size versus age-/sex-matched controls |
|---|---|---|---|---|---|
| 2.2 months | 14 days | Normal | 135 | x 1.5 | x 1.8 |
| 2.3 months | 1 month | Normal | 153 | x 1.2 | x 1.6 |
| 1.8 months | 2.6 months | Normal | 151 | x 2.3 | x 2.4 |
| 2 months | 3.8 months | Normal | 194 | x 2.6 | x 3.4 |
| 5.7 months | 4.1 months | Normal | 136 | x 1.6 | x 2.1 |
| 2.5 months | 4.8 months | Normal | 134 | x 2.4 | x 2.8 |
| 9 months | 5.5 months | Normal | 119 | x 1.7 | x 3.1 |
| 2 months | 5.8 months | Normal | 163 | x 2.1 | x 2.7 |
| 2.3 months | 10.3 months | Normal | 139 | x 2.4 | x 3.3 |

Insulin$^+$ cells in Arx mutants display a β-cell phenotype: To ascertain the identity of the insulin$^+$ cells in Glu-ArxKO and Dox+ IndGlu-ArxKO pancreata, we assayed the expression of several endocrine cell marker genes. Our analyses demonstrated that all insulin$^+$ cells observed in Glu-ArxKO and Dox+ IndGlu-ArxKO pancreata expressed the bone fide β-cell labels Pax4, PC1/3, Glut-2, Pdx1, Nkx6.1, MafA, NeuroD1, HB9, and the pan-endocrine marker Pax6. These were found to lack the α-cell determinants, such as Brn-4 and glucagon, as well as somatostatin or PP (see thereafter and data not shown).

Since these results suggested that the insulin$^+$ cells observed in Glu-ArxKO and Dox+IndGlu-ArxKO pancreata displayed a β-cell phenotype, we sought to ascertain these observations using electron microscopy combined with insulin detection by immunogold labeling. Following the examination of more than 200 sections of pancreas per animal, it appeared that, in both genotypes, all insulin-producing cells displayed a β-cell ultrastructure. Similarly, all cells displaying a β-cell ultrastructure were found to be positive for insulin. Further analyses of endocrine cells in Glu-ArxKO and Dox+ IndGlu-ArxKO outlined a majority of glucagon$^+$, somatostatin$^+$ or PP$^+$ cells abnormally located at a pole of the islet, close to adjacent ducts. Interestingly, quantitative experiments indicated an increase in the number of cells expressing insulin or somatostatin (FIG. 1A, C) and variations in the content of glucagon-producing cells (FIG. 1B). Altogether, our data indicate that the deletion of Arx in α-cells at any age leads to a substantial increase in the insulin+ cell content, such cells displaying most features of true β-cells. In addition, non-β-cells display an abnormal localization within the islet, close to ducts.

α-Cells are converted into β-like cells upon Arx inactivation: To further characterize the effects of the inactivation of Arx in α-cells, we sought to trace their lineage through the analysis of Glu-ArxKO::Rosa pancreata combining XGal staining and immunohistochemical approaches. In Glu-Cre::Rosa control pancreata, β-gal-labeled cells were solely found in the mantle zone of the islets where glucagon+ cells typically reside. Importantly, in Glu-ArxKO::Rosa pancreata, such labeling was also found within the islet core where insulin$^+$ cells are classically detected. By means of immunohistochemistry, a clear expression of the β-galactosidase enzyme was noted in numerous insulin-producing cells, demonstrating a conversion of glucagon-producing cells into insulin-expressing cells. Interestingly, a similar analysis performed in age-matched IndGlu-ArxKO::Rosa animals treated with Dox for one month also outlined numerous insulin$^+$ β-gal$^+$ cells. Of note, the co-detection of β-gal with glucagon or somatostatin expectedly outlined glucagon$^+$ β-gal+ cells while all somatostatin$^+$ cells were found negative for β-gal, suggesting that the supernumerary somatostatin$^+$ cells do not derive from cells having expressed the glucagon hormone. Together, our results providing conclusive evidence that, upon Arx inactivation, α-cells of different ages can also be converted into insulin cells.

While the conversion of α-cells into β-like cells is of interest, it cannot account for the dramatic β-like cell hyperplasia noted in our animal models, nor for the continuous detection of glucagon+ cells despite their conversion. Hence, to gain further insight into the mechanisms underlying these processes, we assayed proliferating cells using immunohistochemical detection of the Ki67 label. Importantly, in Glu-ArxKO pancreata, Ki67$^+$ cells were mostly found located within the ductal lining, close to the non-β-cell cluster. We therefore investigated whether Ngn3 could be re-expressed in animals lacking Arx in α-cells. Indeed, Ngn3 was previously found to be re-expressed in duct-lining cells in animals that underwent pancreatic duct ligation [Xu et al., 2008] or with the forced misexpression of Pax4 in α-cells [Collombat et al., 2009]. Additional work suggested that Ngn3+ cells could be continuously generated and converted into endocrine cells [Xu et al., 2008, Collombat et al., 2009]. Hence, we assayed Glu-ArxKO pancreata for Ngn3 using immunohistochemistry. It should be noted that Ngn3 has been previously observed in endocrine cells [Wang et al., 2009], however, we were not able to detect any Ngn3-producing cells in controls, most likely due to a low expression level. Nevertheless, a clear expression of Ngn3 was noted solely in cells located in the pancreatic ductal lining of animals lacking Arx in α-cells. Importantly, the downstream target of Ngn3, Rfx6 [Soyer et al., 2009], was also found ectopically expressed in the ductal lining of such animals. Taken together, these results provide evidence that, upon α-cell-mediated Arx deficiency, α-cells are converted into β-like cells. This in turn induces continuous regeneration processes characterized by the proliferation of duct-lining cells, the re-expression of the developmental factors Ngn3 and Rfx6, and the compensatory neogenesis of glucagon$^+$ cells, such cells acquiring a β-like cell identity upon glucagon expression and subsequent Arx inactivation.

The sole inactivation of Arx can induce the regeneration of a functional β-cell mass following chemically-induced diabetes: In a continuous effort to ascertain the identity of the supplementary insulin$^+$ cells in animals with α-cell-specific inactivation of Arx, numerous tests were performed. It is important to reiterate that both Glu-ArxKO and Dox+ IndGlu-ArxKO animals displayed normal basal glycemia levels (Tables S1-2). However, upon challenge with a high dose of glucose, these were found to display an improved response with a lower raise in glycemia and a faster return to euglycemia as compared to control animals (FIG. 2A-B). This suggests an improved capacity to release insulin upon glucose stimulation. Indeed, when we combined such glucose challenges with insulin measurements, while the basal insulin levels were found within normal range, a dramatic increase in circulating insulin content was noted when compared to controls (FIG. 2A-B Tables). Our results therefore support the notion of an increased β-like cell mass able to respond to a glucose bolus. Importantly, upon insulin challenge and despite the augmented numbers of β-like cells, the resulting glycemic level variations were found similar in Glu-ArxKO, Dox+ IndGlu-ArxKO, and control animals (FIG. 2C-D). This indicates that, despite a β-like cell hyperplasia, such animals do not develop any insulin resistance.

To determine whether neo-formed insulin+ cells could functionally replace endogenous β-cells, we injected IndGlu-ArxKO animals with a high dose of streptozotocine to obliterate the endogenous β-cell mass. Two groups of IndGlu-ArxKO animals and matching controls were used: the first ("long pre-treatment") corresponding to animals for which Dox treatment was initiated 1.5 months, and the second ("short pre-treatment") 0 to 10 days, prior to streptozotocin administration, Dox treatment being continued for both groups until examination (FIG. 2E-F, respectively). All control animals developed extreme hyperglycemia leading to the death of the majority of these (FIG. 2E-F). Interestingly, all Dox+ IndGlu-ArxKO animals also developed a strong hyperglycemia but none died (FIG. 2E-F). As important was the observation that, following this hyperglycemic phase, a progressive return to normal levels was outlined (FIG. 2E-F). It is interesting to note that a return to euglycemia was also evident when Dox-mediated Arx inactivation in α-cells was triggered as late as on the day of streptozotocin injection (FIG. 2F), suggestive of efficient/rapid mechanisms allowing the restoration of an appropriate glycemic balance.

By immunohistochemical analyses, we observed a clear loss of β-cells shortly after streptozotocin treatment. However, a clear neogenesis was outlined in these Dox+ IndGlu-ArxKO animals, resulting in the replenishment of the β-cell mass. Importantly, when the same experiments were performed on Dox+ IndGlu-ArxKO::Rosa mice, lineage tracing experiments confirmed that most regenerated β-like cells passed through a phase of glucagon expression, suggesting α-cell neogenesis prior to the acquisition of a β-like cell identity upon Arx inactivation. Taken together, these results further demonstrate that the loss of a functional Arx allele in glucagon-producing cells is sufficient to induce their conversion into β-like cells. Our data also suggest that upon such a conversion, compensatory mechanisms are activated and lead to the neogenesis of α-cells, these being again converted into β-like cells upon glucagon expression and thereby Arx inactivation. This cycle of β-like cell regeneration is able to counter toxin-induced diabetes, such cells being able to maintain euglycemia.

The additional inactivation of Pax4 in Arx mutants does not impact the α-cell-mediated β-like cell neogenesis: It was previously shown that the forced expression of Pax4 in glucagon$^+$ cells was sufficient to induce their neogenesis and conversion into β-like cells [Collombat et al., 2009]. Here, we show that, in fact, the inactivation of Arx initiated in embryonic, but also in adult, α-cells is sufficient to induce a similar outcome. One may therefore conclude that the misexpression of Pax4 in α-cells could induce the down-regulation of Arx and thereby trigger α-cell mediated β-like cell neogenesis. However, the opposite could also be true, that is, that the deletion of Arx could promote such processes by upregulating Pax4. To discriminate between these two possibilities, we generated double mutant animals allowing the conditional deletion of Arx and Pax4 specifically in α-cells. To achieve this purpose, we crossed ArxcKO animals with Pax4cKO animals (generated by knock-in of two LoxP sites within the Pax4 locus [Kordowitch et al., 2012]). The resulting double transgenic animals were subsequently crossed with Glu-Cre mice to generate Glu-cre::ArxcKO::Pax4cKO animals (referred to as Glu-ArxKO/Pax4KO). Using immunohistochemistry on 3-month old triple transgenic pancreata, most glucagon-producing cells were found to be negative for both Arx and Pax4. Importantly, a number of insulin-producing cells were also found to lack Pax4, such cells most likely corresponding to α-cells converted into Arx$^{Y/-}$ Pax4$^{-/-}$ β-like cells. Further examination of these triple transgenic pancreata by immunohistochemistry outlined, yet again, a substantial increase in the islet number and a clear islet hypertrophy caused by an insulin+ cell hyperplasia that was found similar to the one observed in animals with Arx deletion. Quantitative analyses confirmed this augmentation in insulin$^+$ cell numbers (FIG. 3A-E), but also in the content in somatostatin$^+$ cells, non-β-cells again being found preferentially located close to ducts within the islets. Of note was the observation that, despite the lack of Pax4 in a majority of β-cells, no alteration in basal glycemia of 6 month-old double mutants could be detected as compared to controls (127±7 mg/dl and 121±4 mg/dl, respectively). Interestingly, upon glucose challenge, Glu-ArxKO/Pax4KO animals displayed a significantly improved response as previously seen in Glu-ArxKO mice (FIG. 3F), suggestive of an increased functional β-like cell mass.

Altogether, our analysis suggests that the combined loss of Arx and Pax4 in glucagon-producing cells results in a phenotype similar to that of Arx mutants, suggesting that Arx represents the main player involved in α-cell-mediated β-like cell neogenesis processes.

Discussion:

In this study, we report that the inactivation of the Arx gene in pancreatic α-cells at different ages results in hypertrophic islets mainly composed of cells displaying a β-cell phenotype. Our data support the notion of a conversion of α-cells into β-like cells upon the sole inactivation of Arx. These processes trigger compensatory mechanisms, associated with the re-expression of Ngn3 and Rfx6, resulting in the neogenesis of α-like cells, such cells being subsequently converted into β-like cells upon glucagon expression and thereby Arx inactivation. Importantly, the newly-formed β-like cells are functional and can reverse chemically-induced diabetes. As interesting was the finding that the additional loss of Pax4 does not impact these mechanisms, suggesting that Arx represents the main inducer of α-cell-mediated β-like cell neogenesis Arx inactivation induces α-cells to acquire a β-like cell identity: We analyzed two transgenic mouse models allowing either (1) the constitutive inactivation of Arx in all glucagon-producing cells as soon as they initiate hormone expression (that is, during embryogenesis), or (2) the inducible loss of Arx in α-cells at any age. In both instances, the inactivation of Arx was found to be fairly efficient with 70-90% of glucagon$^+$ cells appearing Arx-deficient. Interestingly, a number of Arx$^{Y/-}$ glucagon$^+$ cells were found to ectopically express the β-cell-specific gene Pax4. As Pax4 and Arx were previously found to mutually inhibit each other's transcription during the course of pancreas morphogenesis [Collombat et al., 2005], it is conceivable that the loss of Arx may result in Pax4 reactivation in α-cells. Supporting this notion were the phenotypic alterations observed in both models reminiscent of those found in animals with constitutive ectopic expression of Pax4 in glucagon-producing cell [Collombat et al., 2009]. Indeed, a progressive insulin$^+$ cell hyperplasia/islet hypertrophy and a substantial increase in islet numbers were noted. However, unlike in animals misexpressing Pax4 in glucagon$^+$ cells, both Glu-ArxKO and Dox+ IndGlu-ArxKO mice displayed a normal life expectancy, a normal basal glycemia, and a restricted increase in overall islet/insulin$^+$ cell population. These discrepancies can most likely be attributed to differences in the efficiency of the transgene expression, but also, in the case of Dox+ IndGlu-ArxKO, to the fact that Arx deficiency is triggered in α-cells at older ages.

Using lineage tracing, we demonstrate that the loss of Arx in α-cells induces their conversion into cells displaying most features of true β-cells, as outlined through marker gene analyses, electron microscopy examination, and functional assays. It is interesting to note the similarity in phenotypic alterations in Glu-ArxKO and IndGlu-ArxKO animals treated with Dox at different ages. Indeed, this suggests that aging is not a limiting factor to this conversion process, nor to the resulting insulin$^+$ cell neogenesis. In other words, our data indicates that adult α-cells that have been subjected to aging and environmental signals retain their potential for conversion into β-like cells.

Origin of the neo-generated β-like cells: While we demonstrated a conversion of glucagon-producing cells into β-like cells, we also consistently observed the continued presence of α-cells in both animal models and quantification analyses did not show significant variations in their content as compared to controls. This suggests that neogenesis processes are activated in order to compensate for the loss of the converted α-cells. Whether the glucagon shortage provoked by this conversion corresponds to the triggering signal of such neogenesis, as seen in animals misexpressing Pax4 in glucagon+ cells [Collombat et al., 2009], is likely. However, confirming this hypothesis would require further work. Interestingly, numerous proliferating cells were observed in Arx mutant pancreata. These were mostly detected in the ductal lining instead of within the islet. In addition, cells re-activating the expression of the developmental and pro-endocrine gene Ngn3 were also detected in the same location as seen in animals that underwent pancreatic duct ligation [Xu et al. 2008] or with forced misexpression of Pax4 in α-cells [Collombat et al., 2009]. Along the same light, an Ngn3 target, Rfx6, was also found ectopically expressed in the same location, suggesting a recapitulation of, at least, a part of the endocrine differentiation program. Furthermore, an increased number of somatostatin+ cells was observed at a pole of the islet in close proximity to these ducts. Taken together, these results support the notion that, upon the conversion of α-cells into β-like cells, compensatory mechanisms are activated and result in the proliferation of duct-lining cells, the re-expression of Ngn3, as well as the ectopic expression of Rfx6, and the acquisition of an endocrine cell identity. The validation of such a concept would require the inducible tracing of the lineage of Ngn3-/Rfx6-expressing cells. However, due to the use of the Cre/Lox system to inactivate Arx in these animal models, we could not use it to follow the progeny of these cells.

While lineage tracing experiments allowed us to conclude that continuously neogenerated α cells can be converted into β-like cells upon Arx inactivation, the fate/origin of supernumerary somatostatin+ cells remains unclear. Three likely alternatives could be envisioned: (1) Ngn3-re-expressing cells could pass through a transitional phase of glucagon expression prior to adopting one of the different endocrine cell identities, (2) Ngn3-re-expressing cells could preferentially adopt an α-cell fate to replace converted ones and subsequently adopt a β-like cell phenotype upon Arx deficiency, the extra somatostatin+ cells detected corresponding to cells having escaped this lineage favoring, (3) Ngn3-re-expressing cells could give rise to the different endocrine cell subtypes, as seen during the course of development, a number of the neo-generated somatostatin+ cells being subsequently converted into α-like cells to compensate their loss (prior to the acquisition of a β-like cell identity upon Arx inactivation). While the first alternative could be dismissed based on the lack of β-gal labeling of somatostatin+ cells upon glucagon+ cell lineage tracing, the discrimination between the latter hypothesizes will await the generation of proper genetic tools to trace the progeny of somatostatin+ or PP+ cells. Similarly, further work will be required to provide conclusive evidence of the fate/role of Ngn3-reexpressing cells.

The inactivation of Arx in α-cells can reverse the consequences of toxin-induced diabetes: In a continuous effort to ensure the identity of the supplementary β-like cells observed in Glu-ArxKO and Dox+ IndGlu-ArxKO mice, we monitored their physiological parameters and performed functional assays, including glucose and/or insulin level measurements upon glucose or insulin challenges. In all cases, our results support the notion of an increased β-like cell mass capable of responding to different challenges. Of note, despite a β-like cell hyperplasia, these animals were found to exhibit a normal basal glycemia and did not display any insulin resistance, suggestive of a feedback loop allowing optimal regulation despite an increased number of β-like cells. Importantly, our analyses showed that such β-like cells can functionally replace their endogenous counterparts upon streptozotocin-induced β-cell ablation and thereby prevent animal death or chronic hyperglycemia. Interestingly, our data suggest that such regenerative processes can lead to a replenishment of the β-cell mass, and thereby allow animal survival, even when triggered concomitantly with toxin-mediated hyperglycemia. This suggests a relatively efficient and rapid β-like cell neogenesis. Thus, our findings suggest that the sole loss of the Arx gene in α-cells is sufficient to initiate a continuous cycle of α-cell neo-formation and their conversion into β-like cells, and thereby lead to the regeneration a functional β-like cell mass, a concept of importance in the context of diabetes research.

Arx as a main player in β-like cell neogenesis: As mentioned previously, in a number of Glu-ArxKO and Dox+ IndGlu-ArxKO glucagon-producing cells, we noted an ectopic expression of Pax4. While the apparently rapid α-to-β-like cell conversion did not allow us to observe this misexpression in all Arx$^{Y/-}$ glucagon+ cells, one could hypothesize that Pax4 reexpression in α-cells could, at least in part, contribute to their conversion into β-like cells as previously reported [Collombat et al., 2009]. Thus, to conclusively determine whether the forced expression of Pax4 or the inactivation of Arx is at the origin of the conversion of glucagon+ cells into β-like cells, we generated an animal model allowing the inactivation of both genes in glucagon+ cells. Interestingly, we observed phenotypic alterations similar to that of Arx-deficient or Pax4-misexpressing animals [Collombat et al., 2009], including an insulin+ cell hyperplasia, an augmentation in the islet number, and a preferential location of non-β-cells close to ducts. It is worth noting that a number of Pax4− insulin+ cells were observed in these double-mutant pancreata, providing information on their origin and thereby indicating that these were derived from glucagon-producing cells. Thus, these results demonstrate that Pax4 is dispensable from these regeneration processes and allow us to conclude that Arx represents the main factor allowing the conversion of α-cells into β-like cells and their subsequent regeneration. We therefore propose that the development of therapies aiming at inactivating/inhibiting Arx in α-cells could potentially open new avenues for diabetes research and/or aid the design of efficient β-cell differentiation protocols in the context of stem cell research.

EXAMPLE 2

Pharmacological Inhibition of Arx Expression

Material & Methods

Mouse manipulations: Linage tracing experiments were achieved by crossing Glucagon-Cre [Gu et al., 2002; Ashery-Padan et al., 2006; Herrera 2000], Ngn3-CreER [Gu et al., 2002] and HNF-CreER [Gu et al., 2002] animals with ROSA26-β-Gal mouse line [Soriano 1999]. GABA (Sigma) was administered by intraperitoneal injections of a 50 µM solution prepared freshly once a week. Tamoxifen (TAM, Sigma) was dissolved in corn oil at a concentration of 20 mg/ml and administered by gavage. To assess cell proliferation upon GABA addition, WT mice were treated with GABA and subsequently with BrdU for 10 days prior to examination. Cells that had incorporated BrdU during DNA replication were detected by immunohistochemistry (Invitrogen).

Immunohistochemistry: Tissues were fixed in 4% PFA for 30 min at 4° C., embedded in paraffin and 8 µm sections applied to slides. These sections were assayed as described previously [Collombat et al., 2003]. The primary antibodies used were the following: guinea pig polyclonal anti-insulin (1/500-Linco), anti-glucagon (1/500-Milipore), mouse monoclonal anti-glucagon (1/500-Sigma), anti-BrdU (1/40-Roche), anti-E-cadherin (1/200-BD Transduction Lab), rat anti-somatostatin (1/250-Millipore), rabbit anti-Glut2 (1/5000), anti-PC1/3 (1/500-Milipore), anti-Nkx6.1 (1/3000-Novonordisk), anti-Pdx1 (1/1000), anti-NeuroD1 (1/200-Milipore), anti-Ngn3 (1/500-Abgent), anti-β-galactosidase (1/10000-Milipore), chicken anti vimentin (1/5000-Milipore), goat anti-osteopontin (1/200-R&D Systems). The secondary antibodies (1/1000-Molecular Probes) used were: 594- and 488-alexa anti-mouse; 594- and 488-alexa anti-rabbit; 594- and 488-alexa anti-guinea pig; 488-alexa anti-rat; 594- and 488-alexa anti-goat; 594- and 488-alexa anti-chicken. Pictures were processed using ZEISS Axioimager Z1 and LEICA DM 6000 B. For quantification purpose, stained cells were counted manually on every tenth section.

β-galactosidase-based lineage-tracing experiments: Pancreatic tissues were isolated and fixed for 30 min at 4° C. in a solution containing 1% formaldehyde, 0.2% glutaraldehyde, 0.02% NP40. The tissues were dehydrated in 25% sucrose overnight at 4° C. Prior to sectioning, tissues were embedded in freezing medium. For β-galactosidase activity assessment, the tissues were washed in PBS and then incubated overnight in staining solution (500 mM $K_3Fe(CN)_6$, 250 mM $K_4Fe(CN)_6$, 0.5M $MgCl_2$, 40 mg/ml X-gal in DMF).

Cell counts: Quantitative analyses were performed by the counting of colored pixels on (immuno-) stained sections of pancreas using the Photoshop software. Specifically, every $10^{th}$ section was processed using the same settings for all animals and genotypes.

Challenges and blood glucose levels measurement: For challenge purposes, animals were fasted for 16 h and injected intraperitoneally with glucose (2 g/kg of body-weight). Blood glucose levels were measured at the indicated time points post-injection with a ONETOUCH Vita glucometer (Life Scan, Inc., CA).

Induction of streptozotocin-mediated diabetes: To induce hyperglycaemia, STZ (Sigma) was dissolved in 0.1M sodium citrate buffer (pH 4.5), and a single dose was administered intraperitoneally (100 mg/kg) within 10 min of dissolution. Diabetes progression was assessed by the monitoring of blood glucose levels of the mice.

Data Analysis: All values are depicted as mean±SEM and considered significant if P<0.05. Data were statistically analyzed by ANOVA.

Results

The treatment of WT mice with GABA induces an insulin-producing cell hyperplasia, such cells displaying a β-cell phenotype: To determine the consequences of GABA administration, immunohistochemical analyses were performed. GABA-treated WT mice displayed an islet hypertrophy as compared to control mice, resulting from an augmentation in the number of insulin$^+$ cells (Table 2). This increase in islet size appeared to be dependent on the length of GABA treatment (Table 1). We also observed an increase in the number of islets in GABA-treated mice as compared to controls and this increase appeared to be independent of the length of GABA treatment (Table 1). In addition to the increased number of islets and insulin$^+$ cells, WT mice treated with GABA displayed augmented contents of glucagon$^+$ and somatostatin$^+$ cells (Table 2) as compared to their non-treated counterparts. Lastly, GABA-treated animals were found viable, healthy and fertile, their lifespan and basal glycemia remaining within normal range, independent of GABA administration (Table 1).

TABLE 1

Quantitative comparison of the number of islets between GABA-treated animals and aged-matched controls (n = 3 for each group).

| GABA treatment duration | GABA treatment age | Life expectancy | Basal glycemia | Islet count | Islet size |
|---|---|---|---|---|---|
| 1 month | 2.6 m | normal | 126 | x 2.19 ± 0.04 *** | x 1.04 ± 0.15 |
| 2 months | 2.6 m | normal | 134 | x 1.86 ± 0.05 *** | x 2.15 ± 0.22 ** |
| 3 months | 2.6 m | normal | 142 | x 1.80 ± 0.03 *** | x 3.49 ± 0.11 ** |

*** $p < 0.001$,
** $p < 0.01$;
data statistically analyzed by a one-way ANOVA;
all data depicted as mean ± SEM.
The examination of WT mice treated with GABA for 2 or 3 months revealed an increase in the number of hormone-expressing cells and in the number of islets. Life expectancy and basal glycemia (monitored weekly) were found within normal ranges, as compared to controls, in all conditions analyzed.

TABLE 2

Quantitative comparison of the number of glucagon-, insulin- or somatostatin-expressing cells by pixel counting between GABA-treated animals and aged-matched controls (n = 3 for each group).

| GABA treatment duration | Insulin$^+$ cell count | Glucagon$^+$ cell count | Somatostatin$^+$ cell count |
|---|---|---|---|
| 1 month | x 1.04 ± 0.15 | x 0.97 | x 1.43 |
| 2 months | x 2.15 ± 0.22 ** | x 1.91 | x 2.39 |
| 3 months | x 3.49 ± 0.11 ** | x 3.02 | x 2.84 |

*** $p < 0.001$,
** $p < 0.01$;
data statistically analyzed by a one-way ANOVA;
all data depicted as mean ± SEM.
The examination of WT mice treated with GABA for 2 or 3 months revealed an increase in the number of hormone-expressing cells and in the number of islets. Life expectancy and basal glycemia (monitored weekly) were found within normal ranges, as compared to controls, in all conditions analyzed.

To ascertain the identity of the insulin$^+$ cells in GABA-treated pancreata, we assayed the expression of several endocrine cell marker genes by immunochemistry compared to non-treated controls. These analyses revealed that the insulin-expressing cells in the GABA-treated islets displayed most characteristics of true β-cells. Indeed, these cells uniformly expressed the bona fide β-cell markers such as the transcription factors Pdx1, Nkx6.1 and NeuroD1, the β-cell-specific glucose transporter Glut 2, the prohormone convertase 1/3 (PC1/3), as well as the pan-endocrine marker Pax6. These cells were also found to lack the non-β-cell determinants, such as glucagon and somatostatin.

Altogether, our data demonstrate that administration of GABA to WT mice leads to a progressive islet hypertrophy and islet neogenesis. These hypertrophic islets are mainly the consequence of an insulin$^+$ cell hyperplasia (such cells displaying many characteristics of true β-cells) as well as an increase in the glucagon$^+$ cell and somatostatin$^+$ cell content.

GABA treatment can induce the conversion of glucagon-expressing cells into insulin-producing cells: To determine the origin of the islet hypertrophy in GABA-treated mice, further immunohistochemical analyses were performed. Several examples, from unrelated islets, of cells co-expressing insulin with glucagon were noted. This suggests that the processes underlying β-like cell neogenesis could require a transitional phase of glucagon expression. To validate this hypothesis, we used Glu-Cre::Rosa26-lox-β-gal mice. These mice, where glucagon-expressing cells are irreversibly marked, were treated with a high dose of streptozotocin to chemically induce diabetes and then daily injected (or not) with GABA once they were hyperglycemic (glycemia around 300 mg/dl). In Glu-Cre::Rosa26-lox-β-gal controls (not treated with GABA or streptozotocin), using X-gal-staining, β-gal activity was found solely in cells in the mantle zone of the islets where glucagon-expressing cells are classically detected. In the animals treated with GABA (isolated 40 days post-streptozotocin injection), islets appeared regenerated and a large number of β-gal-labeled cells located in the centre of the islets was observed. Further immunohistochemical analyses using antibodies raised against insulin and β-galactosidase outlined a majority of cells positive for insulin and β-galactosidase. It is important to note that such double-positive cells (in lesser proportion) are also observed in GABA-treated Glu-Cre::Rosa26-lox-β-gal animals not subjected to streptozotocin administration. Together, our results provide conclusive evidence that, upon GABA administration and following streptozotocin treatment, β-like cells are regenerated, these deriving from cells that once expressed the glucagon hormone.

Ductal origin of the islet hypertrophy: Despite their conversion into β-like cells, glucagon$^+$ cells are consistently detected, suggesting that these are continuously regenerated. Thus, to gain further insight into the mechanisms underlying these processes, we administered the thymidine analogue 5-bromo-2'-deoxyuridine (BrdU) to detect actively replicating cells. A low number of BrdU-marked cells (mostly insulin-expressing cells) was observed in control mice. Interestingly, most BrdU$^+$ cells were found predominantly located in the ductal lining and in the ductal epithelium of GABA-treated WT pancreata. In addition, glucagon$^+$ and somatostatin$^+$ cells were not uniformly distributed within the islet mantle but rather found clustered at a pole of the islet, adjacent to neighboring ducts, unlike in controls where the distribution of the non-β-cells were found scattered in the mantle of the islets. The atypical location of non-β-cells and the increased cell proliferation observed in the ductal environment, in proximity to islets suggest that a putative source of endocrine precursors exists in that region.

The detection of a small number of cells co-expressing insulin and the duct-specific biomarker osteopontin in islets is consistent with this hypothesis. To confirm their ductal ontogeny, we performed duct-cell lineage tracing experiments on GABA and Tam-treated HNF1β-CreER::Rosa26-lox-β-gal. Following X-gal staining, β-galactosidase activity was detected in cells located within the islet core where insulin$^+$ cells classically reside, while only ducts are labeled with β-galactosidase in controls. These results indicate that duct cells potentially contribute to the islet cell hyperplasia in animals treated with GABA.

Ngn3 re-expression and detection of a mesenchyme-like structure in GABA-treated mice: To further investigate the hypothesis that a potential precursor cell source is located in the ductal region, we examined whether precursor cell markers were expressed. Hence, we assayed GABA-treated pancreata for the developmental pro-endocrine gene Ngn3 using immunohistochemistry. We observed a reactivation of Ngn3 in the ductal environment (ductal lining and ductal epithelium) of GABA-treated pancreata, while no Ngn3 expression was detected in control animals. It is interesting to note that few cells within the islets also express Ngn3 in GABA-treated animals. Lineage tracing experiments were performed to determine the contribution of Ngn3-re-expressing cells to the supplementary endocrine cell mass. In GABA and Tam-treated Ngn3-CreER::Rosa26-lox-β-gal mice, a large number of β-Gal-labeled cells was observed, both in the ductal lining and within the islets, while controls appeared negative for β-galactosidase.

Interestingly, we observed a cell-dense region resembling mesenchyme located near islets and surrounding ducts. In an effort to better characterize those cells, immunohistochemical analyses were undertaken. Vimentin, the canonical mesenchymal marker, was found widely re-expressed in the cell-dense clusters surrounding ducts and close to islets, the same region where Ngn3 was found to be re-expressed. In addition, conversion from vimentin$^+$ to insulin$^+$ or glucagon$^+$ cells was suggested by the presence of a small number of double-positive cells. Altogether, these data indicate that cells re-expressing Ngn3 in GABA-treated mice eventually adopt an endocrine cell identity, such a process possibly involving a mesenchymal to endocrine conversion.

A functional β-cell mass can be regenerated following chemically-induced diabetes in GABA-treated animals: To determine whether neo-formed insulin$^+$ cells could functionally replace endogenous β-cells, we injected WT animals with a high dose of streptozotocin to obliterate the endogenous β-cell mass. Before attaining lethal hyperglycemic levels (approximately 300 mg/dl), the mice were treated either with GABA or with water (controls). While control mice quickly became diabetic and died from extreme hyperglycemia, a steady recovery was observed following a peak in glycemia in WT animals treated with GABA (FIG. 4A).

The glucose responsiveness of the surviving GABA-treated mice was examined. Upon challenge with a high dose of glucose, these animals were found to display an improved response with a lower raise in glycemia and a faster return to euglycemia as compared to controls (non treated with GABA or streptozotocin—FIG. 4B).

By immunohistochemical analyses, a classical loss of β-cells shortly after streptozotocin treatment was observed as compared to sodium citrate treated controls, the only positive insulin staining corresponding to the released insulin from destroyed β-cells. We demonstrated that insulin$^+$ cells were progressively regenerated following β-cell loss in GABA-treated WT animals, by immunohistochemical analyses at different time points.

Our data provide evidence that neo-generated-β-like cells are functional and can counter chemically induced diabetes.

Discussion:

Previous reports have shown a regenerative effect of GABA in TD1 mouse models. However, to our knowledge, no link between GABA and α-cell-mediated-β-cell regeneration has been established. In this study, we sought to investigate whether GABA may be a potential chemical inducer of this process. Using GABA treatment on WT mice and a number of mouse lines allowing lineage tracing, we report that the treatment of WT mice with GABA results in hypertrophic islets due to β-cell, α-cell and δ-cell hyperplasia. We demonstrate that these phenotypic alterations involve the proliferation of cells within the ductal epithelium/lining accompanied by the re-expression of the pro-endocrine factor Ngn3. Taking advantage of our lineage tracing tools, we also show that a majority of the additional cells observed following GABA treatment have passed through a glucagon-, Ngn3- and Hnf1β-expressing stage, further confirming our findings. In addition, the newly-formed cells are functional and can reverse chemically-induced diabetes upon GABA treatment. Taken together, these findings support the notion that GABA can induce β-cell regeneration through an α- to β-cell conversion process.

GABA treatment induces α-cells to convert to β-cells: The phenotypical alterations observed in WT mice treated with GABA for 1 to 3 months are reminiscent of those found in animals with the ectopic expression of Pax4 in glucagon-expressing cells. Indeed, the treatment of WT mice with GABA induces an islet hypertrophy accompanied by an augmentation in hormone cell content and an increase in islet number. One possibility for the origin of the oversized islets could be the proliferation of the endogenous β-cells, this hypothesis being supported by the reports of GABA increasing β-cell replication [Soltani et al., 2011; Ligon et al., 2007]. However, the lack of a significant increase in β-cell proliferation in the GABA-treated mice relative to the size of the islets (data not shown) suggests that the increase in the β-cell population may arise from another source. Taking into account the fact that GABA can convert α-cells into β-like cells in vitro, we used the Glu-Cre::Rosa26-lox-β-gal mouse line to determine the fate of glucagon-producing cells upon GABA addition. Lineage tracing experiments provided evidence for GABA mediated α-to-β-cell conversion in vivo, resulting in hypertrophic islets. In addition, the continued detection of glucagon$^+$ cells despite their conversion suggests that compensatory mechanisms are triggered to regenerate these cells. Indeed, an α-cell renewal was observed as a result of alterations in glucagon signaling or glucagon shortage in previous studies. If, in our case, islet hypertrophy is the consequence of the glucagon depletion and the subsequent α-cell neogenesis, glucagon supplementation should hinder this process. To verify this theory, glucagon could be administrated to GABA-treated WT to observe whether this could diminish the increased number of hormone-expressing cells.

Origin of the islet hypertrophy: Concerning the origin of the neo-generated α-like-cells, the observation of a preferential location of those cells at a pole of islet, adjacent to ducts, re-expression of Ngn3 and increased cell proliferation in the ductal environment hints to a putative source of glucagon-expressing cells. In addition, we noted that few cells within the islets co-expressed Ngn3 and glucagon/insulin (data not shown) further suggesting that those cells passed through a potential Ngn3-re-expressing phase. The tracing of HNF1β$^+$ and Ngn3$^+$ cells in GABA-treated animals supported this hypothesis. Indeed, β-galactosidase activity was detected within the islets in GABA-treated Ngn3-CreER::Rosa26-lox-β-gal and HNF1β-CreER::Rosa26-lox-β-gal mice unlike control animals. However, further immunohistochemical analyses using antibodies raised against endocrine hormones and β-galactosidase should confirm the concept that glucagon-expressing cells (and subsequently insulin-producing cells) passed through a HNF1β$^+$ and Ngn3$^+$ transitional phase. Additional experiments using a Ngn3 conditional knockout mouse line should determine the contribution of Ngn3-re-expressing cells in the regeneration of glucagon$^+$ cells. In addition to Ngn3 re-expression, we observed the expression of a mesenchymal marker, vimentin in the same ductal environment and a few vimentin$^+$ glucagon$^+$/insulin$^+$ cells within the islets. Together, our results suggest that the generation of new epithelial/endocrine cells may require the conversion of mesenchyme-like cells. However, whether the neogenesis of islet cells pass through the activation of a mesenchymal pathway remains to be determined. Furthermore, an increased number of somatostatin$^+$ cells was observed in close proximity to ducts. One could therefore hypothesize that these cells were regenerated upon GABA treatment prior to their conversion into insulin-producing cells. The tracing of somatostatin$^+$ cells should give us answers, however, to our knowledge, a working Somatostatin-Cre mouse line still remains to be generated.

GABA treatment can reverse toxin-induced diabetes: We showed that, following streptozotocin treatment, β-like cells can functionally and progressively replace their endogenous counterparts. The surviving GABA-treated mice were subjected to another round of streptozotocin (data not shown) however, those animals were found to be not sensitive to STZ. A possible explanation is that GABA exerts a protective effect in the β-like cell mass as mentioned by Soltani et al., 2011 or that the neo-generated β-like cells still express some features of α-cells. The mechanisms involved will have to be further investigated.

Molecular mechanisms involved in the conversion of α-cells to β-cells: As previously mentioned, Arx and Pax4 are mutually inhibitory at the transcriptional level [Collombat et al., 2005]. Recently, we have shown that upon Pax4 misexpression, embryonic glucagon-producing cells can be converted into β-like cells in mice [Collombat et al., 2009]. We have herein demonstrated that the inactivation of Arx in glucagon-expressing cells can trigger this process. GABA can induce a decrease in Arx mRNA expression in vitro in α-TC1-6 cell line (FIG. 5).

REFERENCES

Throughout this application, various references describe the state of the art to which this invention pertains. The disclosures of these references are hereby incorporated by reference into the present disclosure.

Ashery-Padan R, Zhou X, Marquardt T, Herrera P, Toube L, et al. (2004) Conditional inactivation of Pax6 in the pancreas causes early onset of diabetes. Developmental biology 269: 479-488.

Belteki, G., Haigh, J., Kabacs, N., Haigh, K., Sison, K., Costantini, F., Whitsett, J., Quaggin, S. E., and Nagy, A. (2005). Conditional and inducible transgene expression in mice through the combinatorial use of Cre-mediated recombination and tetracycline induction. Nucleic Acids Res 33, e51.

Collombat P, Mansouri A, Hecksher-Sørensen J, Serup P, Krull J, Gradwohl G, et al. Opposing actions of Arx and Pax4 in endocrine pancreas development. Genes Dev 2003; 17: 2591-603.

Collombat P, Hecksher-Sørensen J, Broccoli V, Krull J, Ponte I, Mundiger T, et al. The simultaneous loss of Arx and Pax4 genes promotes a somatostatin-producing cell fate specification at the expense of the α- and β-cell lineages in the mouse endocrine pancreas. Development 2005; 132: 2969-80.

Collombat P, Hecksher-Sørensen J, Krull J, Berger J, Riedel D, Herrera P L, et al. Embryonic endocrine pancreas and mature beta cells acquire alpha and PP cell phenotypes upon Arx misexpression. J Clin Invest 2007; 117: 961-70.

Collombat P, Xu X, Ravassard P, Sosa-Pineda B, Dussaud S, Billestrup N, et al. The ectopic expression of Pax4 in the mouse pancreas converts progenitor cells into α and subsequently β-cells. Cell 2009; 138: 449-62.

Fulp, C. T., Cho, G., Marsh, E. D., Nasrallah, I. M., Labosky, P. A., and Golden, J. A. (2008). Identification of Arx transcriptional targets in the developing basal forebrain. Hum Mol Genet 17, 3740-3760. Gomez R, Asnis N, Tannhauser S L, Barros H M (1999) GABA agonists differentially modify blood glucose levels of diabetic rats. Japanese journal of pharmacology 80: 327-331.

Gu G, Dubauskaite J, Melton D A (2002) Direct evidence for the pancreatic lineage: NGN3+ cells are islet progenitors and are distinct from duct progenitors. Development 129: 2447-2457.

Hancock, A. S., Du, A., Liu, J., Miller, M., and May, C. L. (2010). Glucagon deficiency reduces hepatic glucose production and improves glucose tolerance in adult mice. Mol Endocrinol 24, 1605-1614.

Hennighausen L, Wall R J, Tillmann U, Li M, Furth P A (1995) Conditional gene expression in secretory tissues and skin of transgenic mice using the MMTVLTR and the tetracycline responsive system. J Cell Biochem 59: 463-472.

Herrera P L. Adult insulin- and glucagon-producing cells differentiate from two independent cell lineages. Development 2000; 127: 2317-22.

Herrera P L, Huarte J, Zufferey R, Nichols A, Mermillod B, et al. (1994) Ablation of islet endocrine cells by targeted expression of hormone-promoter-driven toxigenes. Proc Natl Acad Sci USA 91: 12999-13003.

Kordowich S, Serup P, Collombat P, Mansouri A (2012) Generation of animals allowing the conditional inactivation of the Pax4 gene. Transgenic Res 21: 1215-1220.

Ligon B, Yang J, Morin S B, Ruberti M F, Steer M L (2007) Regulation of pancreatic islet cell survival and replication by gamma-aminobutyric acid. Diabetologia 50: 764-773.

Mendu S K, Akesson L, Jin Z, Edlund A, Cilio C, et al. (2011) Increased GABA(A) channel subunits expression in CD8(+) but not in CD4(+) T cells in BB rats developing diabetes compared to their congenic littermates. Molecular immunology 48: 399-407.

Nolan A L, O'Dowd J F (2009). The measurement of insulin secretion from isolated rodent islets of Langerhans. Methods Mol Biol. 560:43-51.

Perl A K, Wert S E, Nagy A, Lobe C G, Whitsett J A (2002) Early restriction of peripheral and proximal cell lineages during formation of the lung. Proc Natl Acad Sci USA 99: 10482-10487.

Powers A C, Efrat S, Mojsov S, Spector D, Habener J F, Hanahan D. (1990) Diabetes. 39(4):406-414. Proglucagon processing similar to normal islets in pancreatic alpha-like cell line derived from transgenic mouse tumor.

Quoix N, Cheng-Xue R, Guiot Y, Herrera P L, Henquin J C, et al. (2007) The GluCre-ROSA26EYFP mouse: a new model for easy identification of living pancreatic alpha-cells. FEBS Lett 581: 4235-4240.

Sand F W, Hornblad A, Johansson J K, Loren C, Edsbagge J, et al. (2011) Growthlimiting role of endothelial cells in endoderm development. Dev Biol 352: 267-277.

Slack J M. Developmental biology of the pancreas. Development 1995; 121: 1569-1580.

Soltani N, Qiu H, Aleksic M, Glinka Y, Zhao F, Liu R, Li Y, Zhang N, Chakrabarti R, Ng T, Jin T, Zhang H, Lu W Y, Feng Z P, Prud'homme G J, Wang Q. GABA exerts protective and regenerative effects on islet beta cells and reverses diabetes. Proc Natl Acad Sci USA. 2011 Jul. 12; 108(28): 11692-7. Soriano, P. Generalized LacZ expression with the ROSA26 Cre reporter strain. Nature Genetics 1999; 21: 70-71.

Soyer J, Flasse L, Raffelsberger W, Beucher A, Orvain C, et al. (2010) Rfx6 is an Ngn3-dependent winged helix transcription factor required for pancreatic islet cell development. Development 137: 203-212.

Tian J, Dang H, Kaufman D L (2011) Combining antigen-based therapy with GABA treatment synergistically prolongs survival of transplanted ss-cells in diabetic NOD mice. PloS one 6: e25337.

Tokuyasu K T (1973) A technique for ultracryotomy of cell suspensions and tissues. J Cell Biol 57: 551-565.

Wang S, Jensen J N, Seymour P A, Hsu W, Dor Y, et al. (2009) Sustained Neurog3 expression in hormone-expressing islet cells is required for endocrine maturation and function. Proc Natl Acad Sci USA 106: 9715-9720.

Xu X, D'Hoker J, Stange G, Bonne S, De Leu N, et al. (2008) Beta cells can be generated from endogenous progenitors in injured adult mouse pancreas. Cell 132: 197-207.

The invention claimed is:

1. An in vitro or ex vivo method for producing a population of pancreatic beta-cells, comprising the steps of:
    inhibiting the expression of Aristaless related homeodomain protein (Arx) by contacting a population of pancreatic alpha-cells with Gamma-Amino Butyric Acid (GABA) or a GABA receptor agonist in an amount sufficient to inhibit expression of Arx and induce conversion of the pancreatic alpha-cells to pancreatic beta-cells; and
    confirming that a population of pancreatic beta-cells suitable for administration to a subject is produced by detecting at least one of insulin production upon glucose stimulation, a beta-cell surface antigen, a beta-cell transcription factor, or a beta-cell ultrastructure.

2. The method according to claim 1, with the proviso that the expression of Arx is not inhibited by using a Pax-4 polypeptide or a nucleic acid encoding Pax-4 gene or a vector comprising a nucleic acid encoding Pax-4 gene.

3. The method according to claim 1, wherein the GABA receptor agonist is selected from the group consisting of thiopental, thiamylal, pentobarbital, secobarbital, hexobarbital, butobarbital, amobarbital, barbital, mephobarbital, phenobarbital, primidone, midazolam, triazolam, lometazepam, flutazolam, nitrazepam, fluritrazepam, nimetazepam, diazepam, medazepam, oxazolam, prazeam, tofisopam, rilmazafonoe, lorazepam, temazepam, oxazepam, fluidazepam, chlordiazepoxide, cloxazolam, flutoprazepam, alprazolam, estazolam, bromazepam, flurazepam, clorazepate potassium, haloxazolam, ethyl loflazepate, qazepam, clonazepam, mexazolam, etizolam, brotizolam, clotizaepam, propofol, fospropofol, zolpidem, zopiclone, and exzopiclone.

4. The method according to claim 1 wherein the population of pancreatic alpha-cells is a population of adult pancreatic alpha-cells.

5. The method of claim 1, wherein said beta-cell surface antigen is glucose transporter 2 (GLUT2).

6. The method of claim 1, wherein said beta-cell transcription factor is selected from the group consisting of Pancreatic duodenal homeobox 1 (Pdx 1), NK6 Homeobox 1 (Nkx6.1), MAF transcription factor A (MafA), and Paired Box 4 (Pax4).

7. The method of claim 1, wherein said beta-cell ultrastructure is detected by electron microscopy.

* * * * *